United States Patent
Ku et al.

(10) Patent No.: US 9,138,578 B2
(45) Date of Patent: Sep. 22, 2015

(54) ENDOVASCULAR CATHETERS WITH TUNED CONTROL MEMBERS AND ASSOCIATED SYSTEMS AND METHODS

(71) Applicant: Medtronic Ardian Luxembourg S.a.r.l., Luxembourg (LU)

(72) Inventors: Vincent Ku, Palo Alto, CA (US); Andrew Wu, Los Altos Hills, CA (US)

(73) Assignee: Medtronic Ardian Luxembourg S.a.r.L., Luxembourg (LU)

( * ) Notice: Subject to any disclaimer, the term of this patent is extended or adjusted under 35 U.S.C. 154(b) by 184 days.

(21) Appl. No.: 14/022,306

(22) Filed: Sep. 10, 2013

(65) Prior Publication Data
US 2015/0073514 A1    Mar. 12, 2015

(51) Int. Cl.
*A61B 18/04*    (2006.01)
*A61N 1/28*    (2006.01)
(Continued)

(52) U.S. Cl.
CPC .............. *A61N 1/28* (2013.01); *A61B 18/1492* (2013.01); *A61B 19/00* (2013.01); *A61M 25/0054* (2013.01); *A61B 2017/00309* (2013.01); *A61B 2017/00323* (2013.01); *A61B 2017/00831* (2013.01); *A61B 2017/00867* (2013.01); *A61B 2018/00434* (2013.01); *A61B 2018/00511* (2013.01)

(58) Field of Classification Search
CPC .... A61B 18/12; A61B 18/14; A61B 18/1492; A61B 2018/0196; A61B 2018/00214; A61B 2018/00345; A61B 2018/00404; A61B 2018/00243; A61B 2018/00505–2018/00523; A61B 2018/144; A61B 2018/1467; A61B 2018/1475; A61M 25/0133; A61M 25/0147; A61M 25/005; A61M 25/0052; A61M 25/0058; A61M 25/1033; A61M 25/1044; A61M 25/1058; A61M 2025/0063; A61M 2025/0065

See application file for complete search history.

(56) References Cited

U.S. PATENT DOCUMENTS

| 4,602,624 A | 7/1986 | Naples et al. |
| 4,649,936 A | 3/1987 | Ungar et al. |

(Continued)

FOREIGN PATENT DOCUMENTS

| WO | WO-9525472 | 9/1995 |
| WO | WO-9736548 | 10/1997 |

(Continued)

OTHER PUBLICATIONS

Allen, E.V., Sympathectomy for essential hypertension, Circulation, 1952, 6:131-140.

(Continued)

*Primary Examiner* — Michael Peffley
*Assistant Examiner* — Daniel Fowler

(57) ABSTRACT

Endovascular catheters and control wires for operating the catheters and associated systems, apparatuses, and methods are disclosed include a catheter apparatus having an elongated shaft, a therapeutic assembly at a distal portion of the shaft, and a handle at a proximal portion of the shaft. An actuator is located at the handle and operably coupled to the therapeutic assembly via a tuned control member extending through the shaft. The tuned control member includes a control wire and a tuning component attached to one another within the shaft. The tuned control member is configured to achieve a desired tuned force-displacement response by modifying the stress-strain response that a non-tuned control wire would ordinarily provide without the intervening tuning component.

20 Claims, 25 Drawing Sheets

(51) Int. Cl.
*A61B 18/14* (2006.01)
*A61M 25/00* (2006.01)
*A61B 19/00* (2006.01)
*A61B 17/00* (2006.01)
*A61B 18/00* (2006.01)

(56) References Cited

U.S. PATENT DOCUMENTS

| | | | |
|---|---|---|---|
| 4,764,504 A | 8/1988 | Johnson et al. |
| 4,976,711 A | 12/1990 | Parins et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,484,400 A | 1/1996 | Edwards et al. |
| 5,571,147 A | 11/1996 | Sluijter et al. |
| 5,588,964 A | 12/1996 | Imran et al. |
| 5,599,345 A | 2/1997 | Edwards et al. |
| 5,626,576 A | 5/1997 | Janssen |
| 5,672,174 A | 9/1997 | Gough et al. |
| 5,688,266 A | 11/1997 | Edwards et al. |
| 5,700,282 A | 12/1997 | Zabara |
| 5,707,400 A | 1/1998 | Terry, Jr. et al. |
| 5,772,590 A | 6/1998 | Webster, Jr. |
| 5,865,787 A | 2/1999 | Shapland et al. |
| 5,893,885 A | 4/1999 | Webster et al. |
| 5,944,710 A | 8/1999 | Dev et al. |
| 5,954,719 A | 9/1999 | Chen et al. |
| 5,983,141 A | 11/1999 | Sluijter et al. |
| 6,004,269 A | 12/1999 | Crowley et al. |
| 6,009,877 A | 1/2000 | Edwards |
| 6,066,134 A | 5/2000 | Eggers et al. |
| 6,099,524 A | 8/2000 | Lipson et al. |
| 6,117,101 A | 9/2000 | Diederich et al. |
| 6,135,999 A | 10/2000 | Fanton et al. |
| 6,149,620 A | 11/2000 | Baker et al. |
| 6,161,048 A | 12/2000 | Sluijter et al. |
| 6,219,577 B1 | 4/2001 | Brown, III et al. |
| 6,224,592 B1 | 5/2001 | Eggers et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,405,732 B1 | 6/2002 | Edwards et al. |
| 6,413,255 B1 | 7/2002 | Stern |
| 6,488,679 B1 | 12/2002 | Swanson et al. |
| 6,506,189 B1 | 1/2003 | Rittman, III et al. |
| 6,514,226 B1 | 2/2003 | Levin et al. |
| 6,522,926 B1 | 2/2003 | Kieval et al. |
| 6,542,781 B1 | 4/2003 | Koblish et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,685,648 B2 | 2/2004 | Flaherty et al. |
| 6,711,444 B2 | 3/2004 | Koblish |
| 6,736,835 B2 | 5/2004 | Pellegrino et al. |
| 6,845,267 B2 | 1/2005 | Harrison et al. |
| 6,850,801 B2 | 2/2005 | Kieval et al. |
| 6,885,888 B2 | 4/2005 | Rezai |
| 6,893,436 B2 | 5/2005 | Woodard et al. |
| 6,939,346 B2 | 9/2005 | Kannenberg et al. |
| 7,149,574 B2 | 12/2006 | Yun et al. |
| 7,162,303 B2 | 1/2007 | Levin et al. |
| 7,221,979 B2 | 5/2007 | Zhou et al. |
| 7,381,200 B2 | 6/2008 | Katoh et al. |
| 7,390,894 B2 | 6/2008 | Weinshilboum et al. |
| 7,617,005 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,778,703 B2 | 8/2010 | Gross et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2002/0165532 A1 | 11/2002 | Hill et al. |
| 2002/0183682 A1 | 12/2002 | Darvish et al. |
| 2003/0050681 A1 | 3/2003 | Pianca et al. |
| 2003/0060858 A1 | 3/2003 | Kieval et al. |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2004/0010289 A1 | 1/2004 | Biggs et al. |
| 2004/0215186 A1 | 10/2004 | Cornelius et al. |
| 2005/0080409 A1 | 4/2005 | Young et al. |
| 2005/0187579 A1 | 8/2005 | Danek et al. |
| 2005/0228460 A1 | 10/2005 | Levin et al. |
| 2006/0095029 A1 | 5/2006 | Young et al. |
| 2006/0206150 A1 | 9/2006 | Demarais et al. |
| 2006/0271111 A1 | 11/2006 | Demarais et al. |
| 2007/0129720 A1 | 6/2007 | Demarais et al. |
| 2007/0265687 A1 | 11/2007 | Deem et al. |
| 2008/0319513 A1 | 12/2008 | Pu et al. |
| 2009/0036948 A1 | 2/2009 | Levin et al. |
| 2010/0137860 A1 | 6/2010 | Demarais et al. |
| 2010/0137952 A1 | 6/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2012/0130289 A1 | 5/2012 | Demarais et al. |
| 2012/0130345 A1 | 5/2012 | Levin et al. |
| 2012/0172837 A1 | 7/2012 | Demarais et al. |

FOREIGN PATENT DOCUMENTS

| | | |
|---|---|---|
| WO | WO-0122897 | 4/2001 |
| WO | WO-0170114 | 9/2001 |
| WO | WO-2005030072 | 4/2005 |
| WO | WO-2005041748 | 5/2005 |
| WO | WO-2005110528 | 11/2005 |
| WO | WO-2006041881 | 4/2006 |
| WO | WO-2007008954 | 1/2007 |

OTHER PUBLICATIONS

Bello-Reuss, E. et al., "Effects of Acute Unilateral Renal Denervation in the Rat," Journal of Clinical Investigation, vol. 56, Jul. 1975, pp. 208-217.

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.

Bhandari, A. and Ellias, M., "Loin Pain Hematuria Syndrome: Pain Control with RFA to the Splanchanic Plexus," The Pain Clinc, 2000, vol. 12, No. 4, pp. 323-327.

Curtis, John J. et al., "Surgical Therapy for Persistent Hypertension After Renal Transplantation" Transplantation, 31:125-128 (1981).

Dibona, Gerald F. et al., "Neural Control of Renal Function," Physiological Reviews, vol. 77, No. 1, Jan. 1997, The American Physiological Society 1997, pp. 75-197.

Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.

Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.

Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.

(56) References Cited

OTHER PUBLICATIONS

Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul lntegr Comp Physiol 1997, vol. 272, 1997 the American Physiological Society, pp. 2034-2039.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).

Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.

(56) References Cited

OTHER PUBLICATIONS

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.

"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.

"Iberis—Renal Sympathetic Denervation System: Turning innovation into quality care." [Brochure], Terumo Europe N.V., 2013, Europe, 3 pages.

"Neurotech Reports Announces Winners of Gold Electrode Awards." Neurotech business report, 2009. 1 page. <http://www.neurotechreports.com/pages/goldelectrodes09.html>.

"Quick. Consistent. Controlled. OneShot renal Denervation System" [Brochure], Covidien: positive results for life, 2013, (n.l.), 4 pages.

"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.

"The Edison Awards™" Edison Awards: Honoring Innovations & Innovators, 2013, 2 pages, <http://www.edisonawards.com/Awards.php>.

"The Future of Renal denervation for the Treatment of Resistant Hypertension." St. Jude Medical, Inc., 2012, 12 pages.

"Vessix Renal Denervation System: So Advanced Its Simple." [Brochure], Boston Scientific: Advancing science for life, 2013, 6 pages.

Asbell, Penny, "Conductive Keratoplasty for the Correction of Hyperopia." Tr Am Ophth Soc, 2001, vol. 99, 10 pages.

Badoer, Emilio, "Cardiac afferents play the dominant role in renal nerve inhibition elicited by volume expansion in the rabbit." Am J Physiol Regul Integr Comp Physiol, vol. 274, 1998, 7 pages.

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.

Benito, F., et al. "Radiofrequency catheter ablation of accessory pathways in infants." Heart, 78:160-162 (1997).

Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.

Bohm, Michael et al., "Rationale and design of a large registry on renal denervation: the Global Symplicity registry." EuroIntervention, vol. 9, 2013, 9 pages.

Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.

Davis, Mark et al., "Effectiveness of Renal Denervation Therapy for Resistant Hypertension." Journal of the American College of Cardiology, vol. 62, No. 3, 2013, 11 pages.

Dibona, G.F. "Sympathetic nervous system and kidney in hypertension." Nephrol and Hypertension, 11: 197-200 (2002).

Dubuc, M., et al., "Feasibility of cardiac cryoablation using a transvenous steerable electrode catheter." J Interv Cardiac Electrophysiol, 2:285-292 (1998).

Final Office Action; U.S. Appl. No. 12/827,700; Mailed on Feb. 5, 2013, 61 pages.

Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.

Gelfand, M., et al., "Treatment of renal failure and hypertension." U.S. Appl. No. 60/442,970, filed Jan. 29, 2003, 23 pages.

Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.

Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).

Hall, W. H., et al. "Combined embolization and percutaneous radiofrequency ablation of a solid renal tumor." *Am. J. Roentgenol*,174: 1592-1594 (2000).

Han, Y.-M, et al., "Renal artery ebolization with diluted hot contrast medium: An experimental study." J Vasc Interv Radiol, 12: 862-868 (2001).

Hansen, J. M., et al. "The transplanted human kidney does not achieve functional reinnervation." *Clin. Sci*, 87: 13-19 (1994).

Hendee, W. R. et al. "Use of Animals in Biomedical Research: The Challenge and Response." *American Medical Association White Paper* (1988) 39 pages.

Hering, Dagmara et al., "Chronic kidney disease: role of sympathetic nervous system activation and potential benefits of renal denervation." EuroIntervention, vol. 9, 2013, 9 pages.

Huang et al., "Renal denervation prevents and reverses hyperinsulinemia-induced hypertension in rats." Hypertension 32 (1998) pp. 249-254.

Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.

Kaiser, Chris, AHA Lists Year's Big Advances in CV Research, medpage Today, Dec. 18, 2012, 4 pages, <http://www.medpagetoday.com/Cardiology/PCI/36509>.

Kompanowska, E., et al., "Early Effects of renal denervation in the anaesthetised rat: Natriuresis and increased cortical blood flow." J Physiol, 531. 2:527-534 (2001).

Lee, S.J., et al. "Ultrasonic energy in endoscopic surgery." Yonsei Med J, 40:545-549 (1999).

Linz, Dominik et al., "Renal denervation suppresses ventricular arrhythmias during acute ventricular ischemia in pigs." Heart Rhythm, vol. 0, No. 0, 2013, 6 pages.

Lustgarten, D.L.,et al., "Cryothermal ablation: Mechanism of tissue injury and current experience in the treatment of tachyarrhythmias." Progr Cardiovasc Dis, 41:481-498 (1999).

Mabin, Tom et al., "First experience with endovascular ultrasound renal denervation for the treatment of resistant hypertension." EuroIntervention, vol. 8, 2012, 5 pages.

Mahfoud, Felix et al., "Ambulatory Blood Pressure Changes after Renal Sympathetic Denervation in Patients with Resistant Hypertension." Circulation, 2013, 25 pages.

Mahfoud, Felix et al., "Expert consensus document from the European Society of Cardiology on catheter-based renal denervation." European Heart Journal, 2013, 9 pages.

Mahfoud, Felix et al., "Renal Hemodynamics and Renal Function After Catheter-Based Renal Sympathetic Denervation in Patients With Resistant Hypertension." Hypertension, 2012, 6 pages.

Medical-Dictionary.com, Definition of "Animal Model," http://medical-dictionary.com (search "Animal Model"), 2005, 1 page.

Medtronic, Inc., Annual Report (Form 10-K) (Jun. 28, 2011) 44 pages.

Millard, F. C., et al, "Renal Embolization for ablation of function in renal failure and hypertension." Postgraduate Medical Journal, 65, 729-734, (1989).

Oliveira, V., et al., "Renal denervation normalizes pressure and baroreceptor reflex in high renin hypertension in conscious rats." Hypertension, 19:II-17-II-21 (1992).

(56) References Cited

OTHER PUBLICATIONS

Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversible renal deneravation on haemodynamic and excretory functions on the ipsilateral and contralateral kidney in the cat." Hypertension, 4:181-188 (1986).
Stouffer, G. A. et al., Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium rentention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Beale et al., "Minimally Invasive Treatment for Varicose Veins: A Review of Endovenous Laser Treatment and Radiofrequency Ablation". Lower Extremity Wounds 3(4), 2004, 10 pages.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.

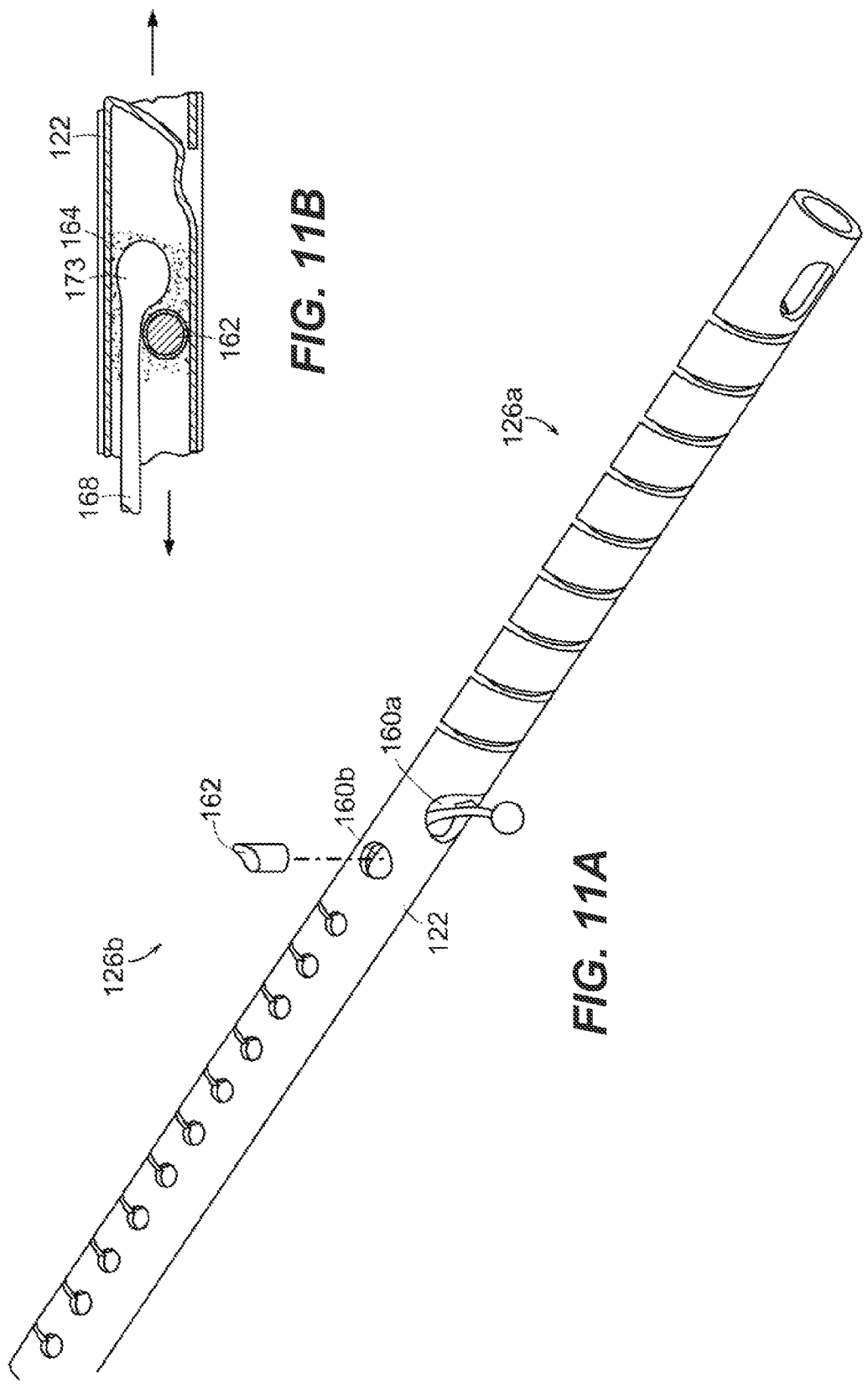

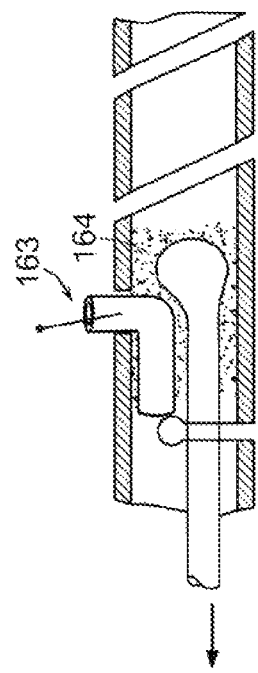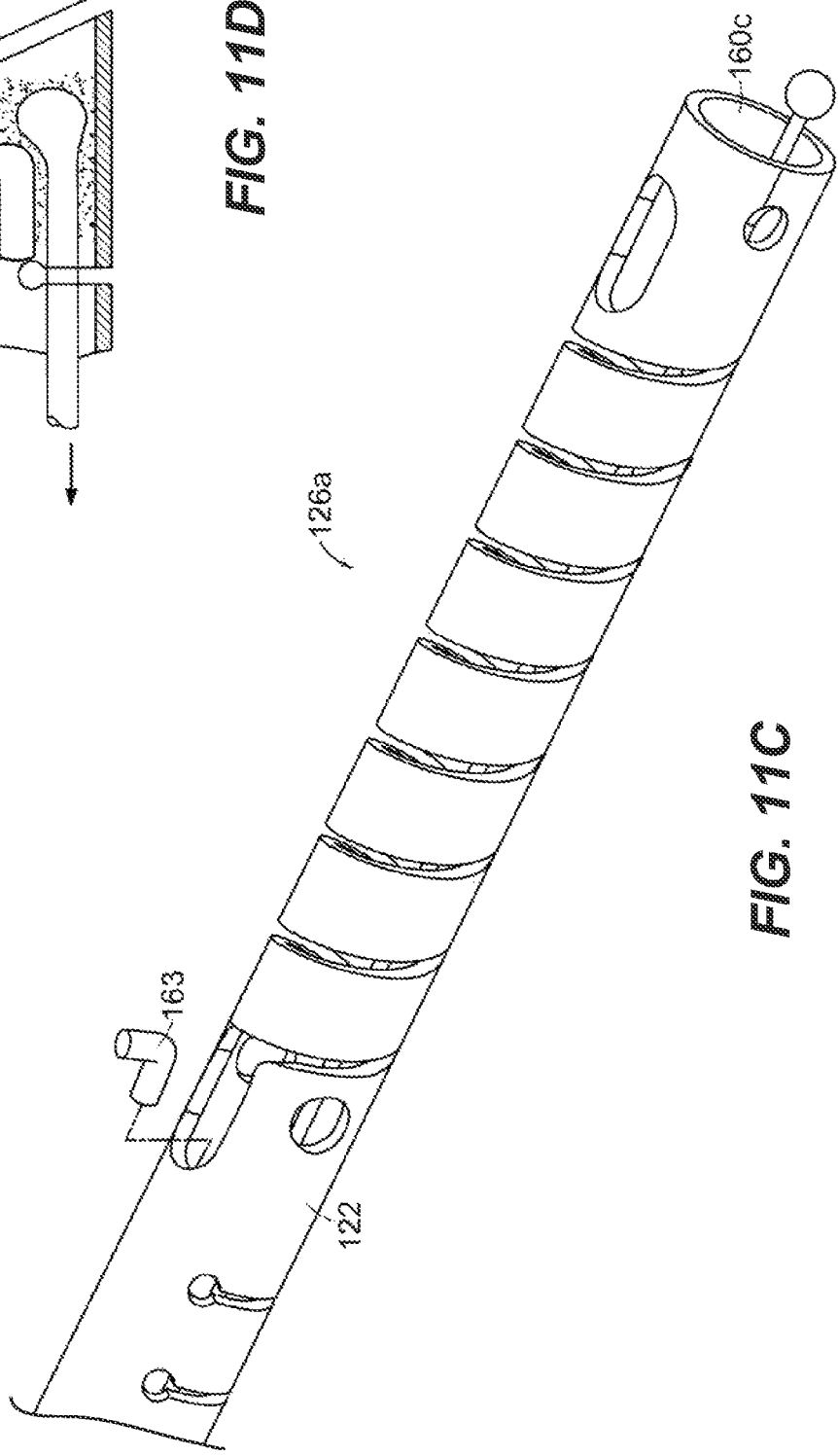

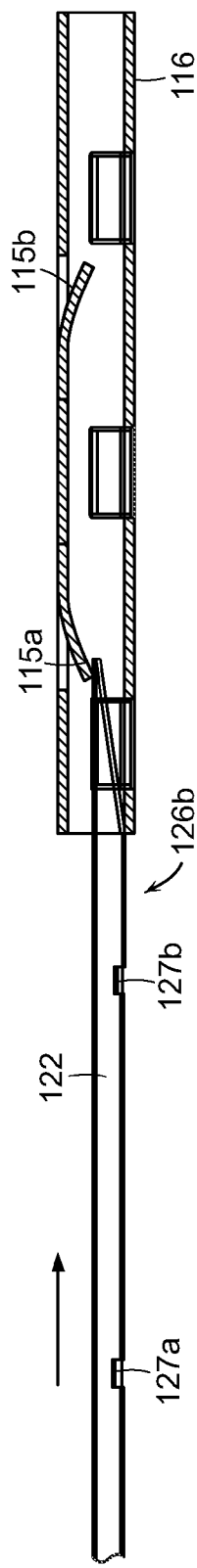
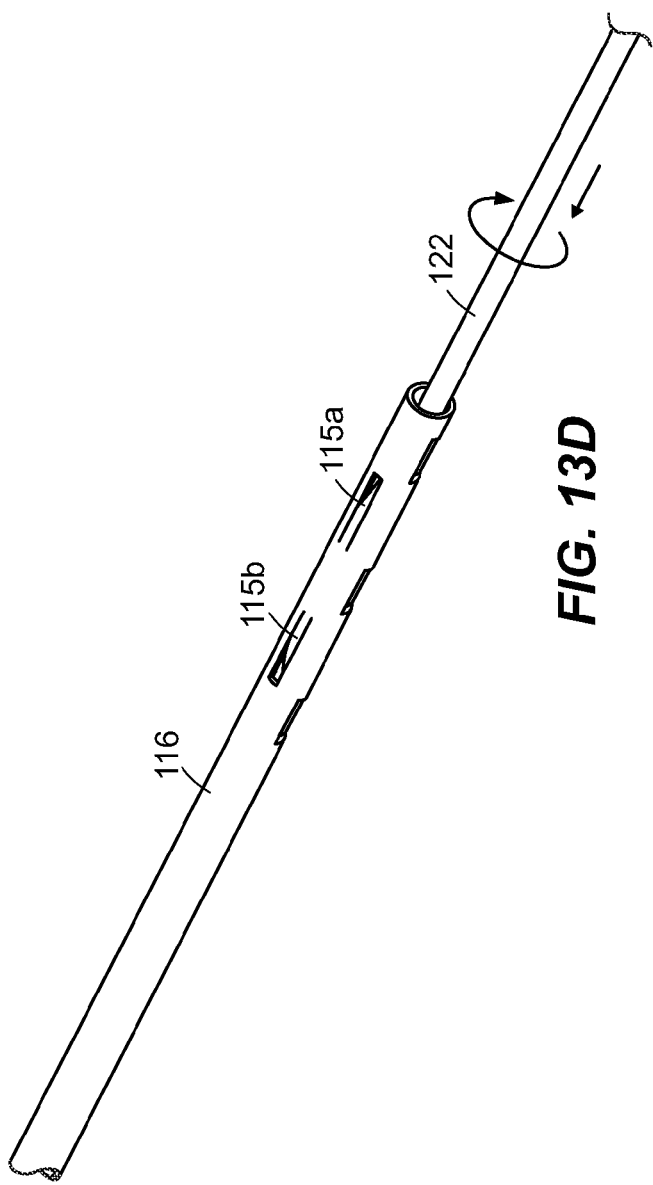
FIG. 13C
FIG. 13D

*Arterial Vasculature*

*Venous Vasculature*

ENDOVASCULAR CATHETERS WITH TUNED CONTROL MEMBERS AND ASSOCIATED SYSTEMS AND METHODS

TECHNICAL FIELD

The present technology relates generally to endovascular catheters that employ control wires and associated systems and methods. In particular, several embodiments are directed to tuned control members employed in endovascular intraoperative renal nerve modulation devices and associated systems and methods.

BACKGROUND

The sympathetic nervous system (SNS) is a primarily involuntary bodily control system typically associated with stress responses. Fibers of the SNS innervate tissue in almost every organ system of the human body and can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. For example, radiotracer dilution has demonstrated increased renal norepinephrine (NE) spillover rates in patients with essential hypertension.

Cardio-renal sympathetic nerve hyperactivity can be particularly pronounced in patients with heart failure. For example, an exaggerated NE overflow from the heart and kidneys to plasma is often found in these patients. Heightened SNS activation commonly characterizes both chronic and end stage renal disease. In patients with end stage renal disease, NE plasma levels above the median have been demonstrated to be predictive for cardiovascular diseases and several causes of death. This is also true for patients suffering from diabetes or contrast nephropathy. Evidence suggests that sensory afferent signals originating from diseased kidneys are major contributors to initiating and sustaining elevated central sympathetic outflow.

Sympathetic nerves innervating the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release), calcium channel blockers and vasodilators (to counteract peripheral vasoconstriction caused by increased sympathetic drive), aldosterone blockers (to block the actions of increased aldosterone released from activation of the renin-angiotensin-aldosterone system), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIGS. 11A-11J illustrate various anchoring configurations of a control member at a location between distal and proximal regions of the support structure in accordance with embodiments of the present technology.

FIGS. 13A-13D illustrate various configurations for attaching a portion of an elongated shaft to a support member in accordance with embodiments of the present technology.

DETAILED DESCRIPTION

The present technology is directed to endovascular catheters and associated systems, apparatuses, and methods. In one aspect, the present technology is directed to endovascular catheters that operate with a "tuned" control member as will be described below. In another aspect, the present technology is directed to treatment assemblies configured to expand in transverse dimension (e.g., helically or spirally expand) as well as features that can facilitate such operation. Further, certain embodiments are directed to apparatuses, systems, and methods for achieving electrically- and/or thermally-induced renal neuromodulation (i.e., rendering neural fibers that innervate the kidney inert or inactive or otherwise completely or partially reduced in function) by percutaneous transluminal intravascular access.

A person of ordinary skill with appreciate, however, that other applications and other embodiments are within the scope of the present technology. For example, other embodiments can include monitoring, therapeutic, or other treatment applications. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described below with reference to FIGS. 1-17B.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. SELECTED EMBODIMENTS OF CATHETER SYSTEMS

Figure 1:
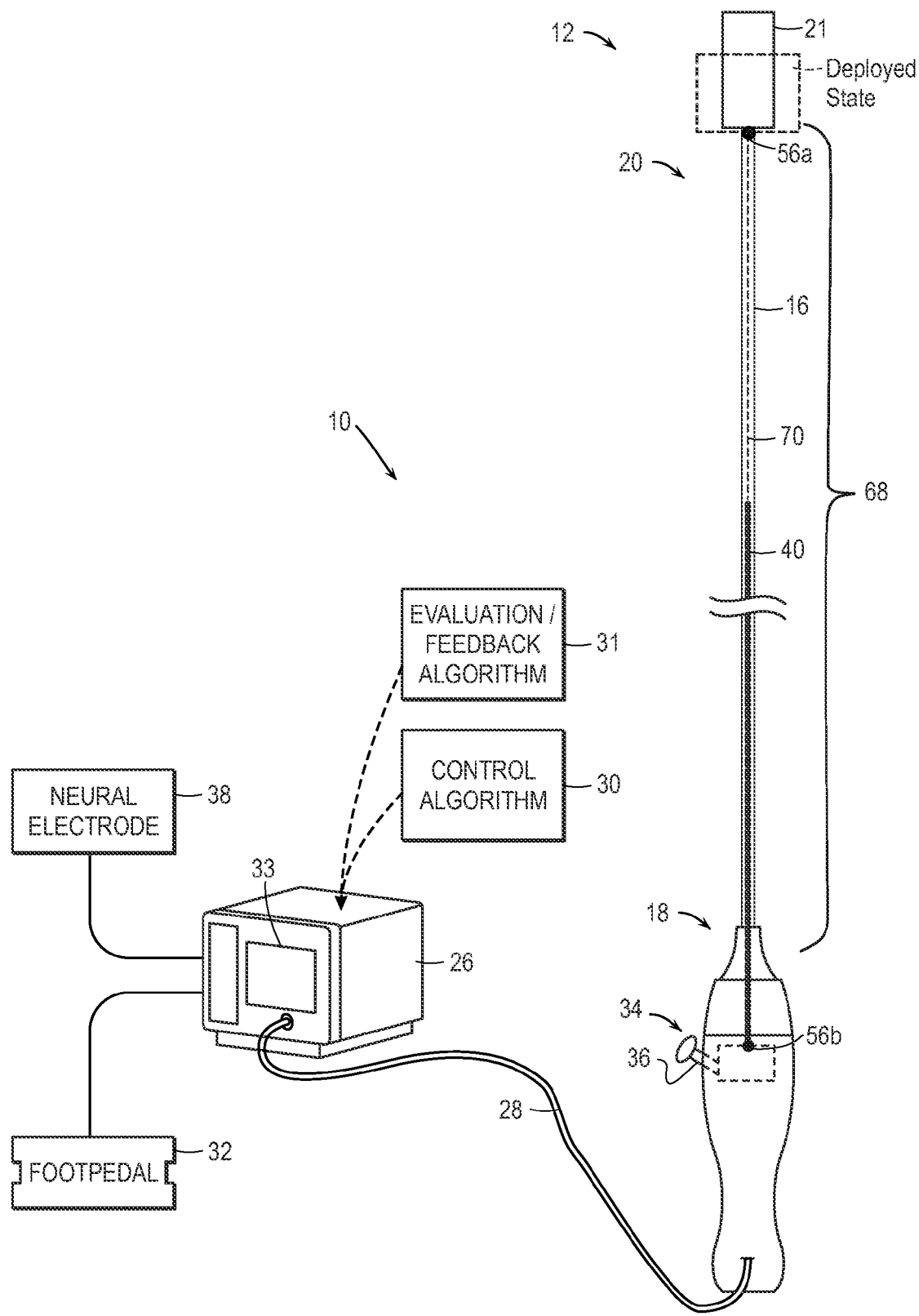
FIG. 1 illustrates a catheter system configured in accordance with an embodiment of the present technology.

FIG. 1 illustrates a catheter system 10 ("system 10") configured in accordance with an embodiment of the present technology. The system 10 includes a treatment device 12 (e.g., a catheter assembly) including an elongated shaft 16 and a handle 34 at a proximal region of a proximal end portion 18 of the shaft 16. The treatment device 12 also includes a therapeutic assembly 21 at a distal end portion 20 of the shaft 16 that extends distally relative to the proximal end portion 18. The therapeutic assembly 21, for example, can be attached to the distal end portion 20 and/or define a section of the distal end portion 20.

The therapeutic assembly 21 is operably coupled to the actuator 36 by a tuned control member 68. The therapeutic assembly 21 is configured to transform from a delivery state to a deployed state, and to return from the deployed state to the delivery state by the operation of an actuator 36 such as a knob, pin, or lever carried by a handle 34. In other embodiments, however, the therapeutic assembly 21 may be transformed between the delivery and deployed states using other suitable mechanisms or techniques.

The delivery state can include, for example, a low profile arrangement to facilitate delivery (e.g., insertion), removal, and in certain modalities, repositioning of the therapeutic assembly 21 at a treatment site. Upon delivery to the treatment site, the therapeutic assembly 21 can be transformed to the deployed state (e.g., a radially expanded, longitudinally contracted, deflected, curved, or other transformed state) for delivering a therapeutic treatment. The shaft 16 can also be configured to transform in some embodiments. For example, the shaft 16 can have articulated segments (not shown) that bend in response to proximal displacement of the tuned control member 68. In some of the embodiments described in further detail below, the therapeutic assembly 21 may expand in transverse dimension (e.g., helically/spirally) when deployed. Embodiments of such assemblies are further disclosed in U.S. patent application Ser. No. 13/281,360, filed Oct. 25, 2011, and which is incorporated by reference herein in its entirety. Alternatively, the deployed state may involve other forms of expansion that are non-helical or non-spiral. In some embodiments, the deployed state can involve expanding the therapeutic assembly 21 in at least one direction (e.g., transverse to the elongated axis of the shaft 16), while simultaneously contracting in at least one other direction (e.g., parallel with the elongated axis of the shaft 16). In other embodiments, however, the deployed state expansion can occur without any simultaneous contraction.

Continuing with reference to FIG. 1, the tuned control member 68 extends from the handle 34 through a passageway in the elongated shaft 16 to the distal end portion 20. As shown, the tuned control member 68 is attached at a first distal attachment location 56a at, within, or near the therapeutic assembly 21 (e.g., at the distal tip) and a second proximal attachment location 56b (at or near the actuator 36). For purposes of illustration, the tuned control member 68 is shown as including a wire 70 (drawn in broken lines) and a tuning component 40 (drawn as a thicker, dark line) operably coupled to the wire 70. As described in greater detail below, however, the wire 70 and/or the tuning component 40 may have different configurations in other embodiments.

In operation, the tuned control member 68 is configured to apply a tensile or other suitable force to the therapeutic assembly 21 by displacement of the tuned control member 68, such as by displacement of the tuned control member 68 towards the handle 34. For example, the actuator 36 can be operated to create a tensile force by proximally displacing one end of the tuned control member 68 along the longitudinal axis of the shaft. As described in greater detail below, the tuned control member 68 is configured to provide a desired tensile force for a given displacement of the tuned control member 68.

In various embodiments, the system 10 can include other components. In the illustrated embodiment, for example, the system 10 includes an energy source or console 26. The energy source or console 26 may be configured to generate a selected form and magnitude of energy for delivery to the target treatment site via the therapeutic assembly 21. A control mechanism, such as foot pedal 32, may be connected (e.g., pneumatically connected or electrically connected) to the console to allow the operator to initiate, terminate and, optionally, adjust various operational characteristics of the energy generator, including, but not limited to, power delivery. The system 10 may also include a remote control device (not shown) that can be positioned in a sterile field and operably coupled to the therapeutic assembly 21. The remote control device is configured to allow for selective activation of the therapeutic assembly 21. In other embodiments, the remote control device may be built into the handle 34. The energy source 26 can be configured to deliver the treatment energy via an automated control algorithm 30 and/or under the control of the clinician. In addition, the energy source 26 may include one or more evaluation or feedback algorithms 31 to provide feedback to the clinician before, during, and/or after therapy.

The energy source 26 can further include processing circuitry, such as a microprocessor, and a display 33 (e.g., a monitor). The processing circuitry may be configured to execute stored instructions relating to a control algorithm. The energy source 26 may be configured to communicate with the treatment device 12 (e.g., via the cable 28) to control the neuromodulation assembly and/or to send signals to or receive signals from the therapeutic assembly 21. The display 33 may be configured to provide indications of power levels or sensor data, such as audio, visual or other indications, or may be configured to communicate the information to another device. For example, the energy source 26 may also be configured to be operably coupled to a catheter lab screen or system for displaying treatment information, such as nerve activity before and after treatment.

As described in greater detail below, in one embodiment the system 10 is a renal neuromodulation system, the treatment device 12 is an intravascular treatment device, and the therapeutic assembly 21 can include a neuromodulation assembly (e.g., one or more electrodes or energy delivery elements) configured to be delivered endovascularly to a treatment site within the vasculature (e.g., a renal artery).

II. RENAL NEUROMODULATION

Renal neuromodulation is the partial or complete incapacitation or other effective disruption of nerves innervating the kidneys. In particular, renal neuromodulation comprises inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks).

Renal neuromodulation is expected to efficaciously treat several clinical conditions characterized by increased overall sympathetic activity, and in particular conditions associated with central sympathetic over stimulation such as hypertension, heart failure, acute myocardial infarction, metabolic syndrome, insulin resistance, diabetes, left ventricular hypertrophy, chronic and end stage renal disease, inappropriate fluid retention in heart failure, osteoporosis, cardio-renal syndrome, and sudden death. The reduction of afferent neural signals contributes to the systemic reduction of sympathetic tone/drive, and renal neuromodulation is expected to be useful in treating several conditions associated with systemic sympathetic over activity or hyperactivity. Renal neuromodulation can potentially benefit a variety of organs and bodily structures innervated by sympathetic nerves. For example, a reduction in central sympathetic drive may reduce insulin resistance that afflicts patients with metabolic syndrome and Type II diabetics.

Various techniques can be used to partially or completely incapacitate neural pathways, such as those innervating the kidney. The purposeful application of energy (e.g., electrical energy, thermal energy) to tissue by energy delivery element(s) can induce one or more desired thermal heating effects on localized regions of the renal artery and adjacent regions of the renal plexus, which lay intimately within or adjacent to the adventitia of the renal artery. The purposeful application of the thermal heating and cooling effects can achieve neuromodulation along all or a portion of the renal plexus.

More specifically, exposure to thermal energy (heat) in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity (RSNA) is expected.

Figure 2:
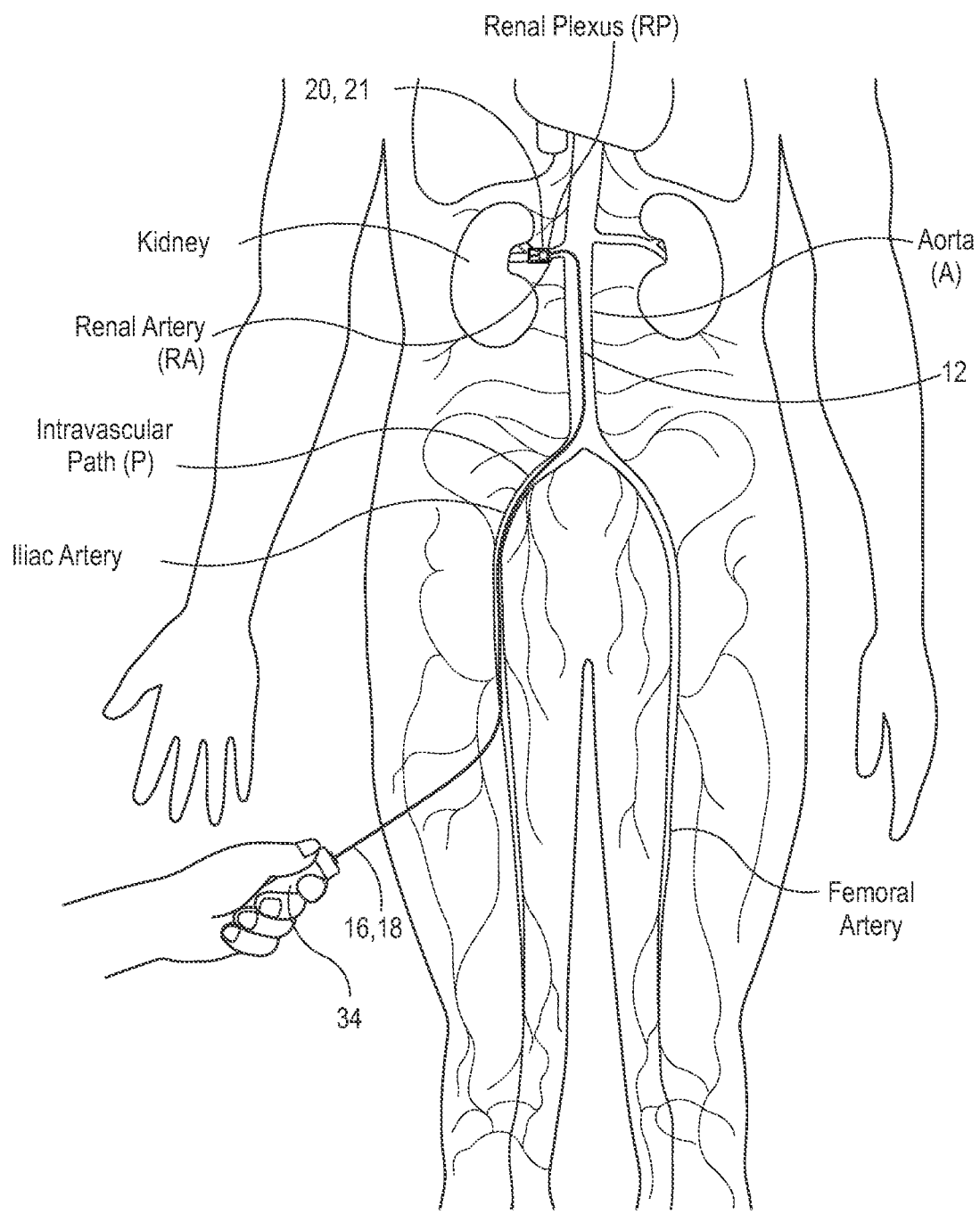
FIG. 2 illustrates modulating renal nerves with a neuromodulation system configured in accordance with an embodiment of the present technology.

FIG. 2 illustrates modulating renal nerves with an embodiment of the system 10. The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal end portion 18 of the elongated shaft 16 is exposed externally of the patient. By manipulating the proximal end portion 18 of the elongated shaft 16 from outside the intravascular path P, the clinician may advance the elongated shaft 16 through the sometimes tortuous intravascular path P and remotely manipulate the distal end portion 20 of the elongated shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12 itself.

After the therapeutic assembly 21 is adequately positioned in the renal artery RA, it can be expanded using the actuator 36 or other suitable means until the neuromodulation assembly is positioned at its target site and the therapeutic assembly is in stable contact with the inner wall of the renal artery RA. The purposeful application of energy from the neuromodulation assembly is then applied to tissue to induce one or more desired neuromodulating effects on localized regions of the renal artery and adjacent regions of the renal plexus RP, which lay intimately within, adjacent to, or in close proximity to the adventitia of the renal artery RA. The purposeful application of the energy may achieve neuromodulation along all or at least a portion of the renal plexus RP.

Figure 3A:
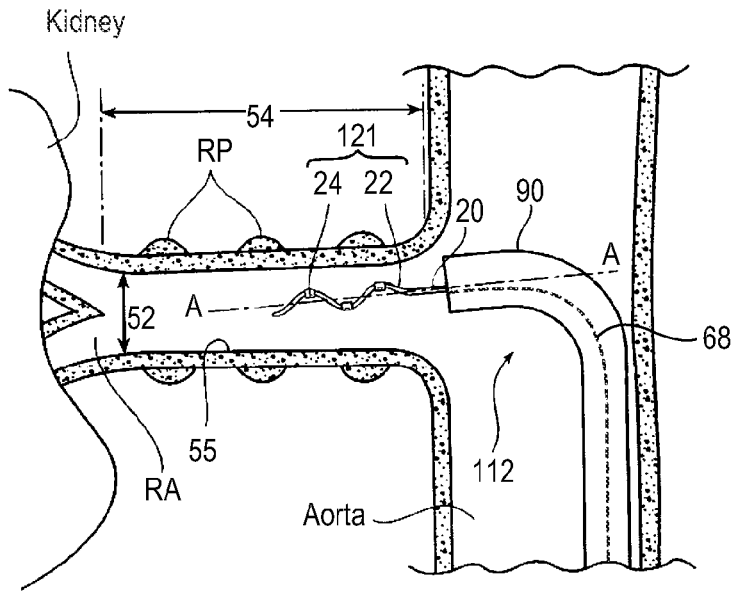
FIGS. 3A-3C illustrate a treatment device having a therapeutic assembly positioned at a renal artery and helical or spiral expansion of the therapeutic assembly from a delivery state to a deployed (or expanded) state in accordance with an embodiment of the present technology.
Figure 3B:
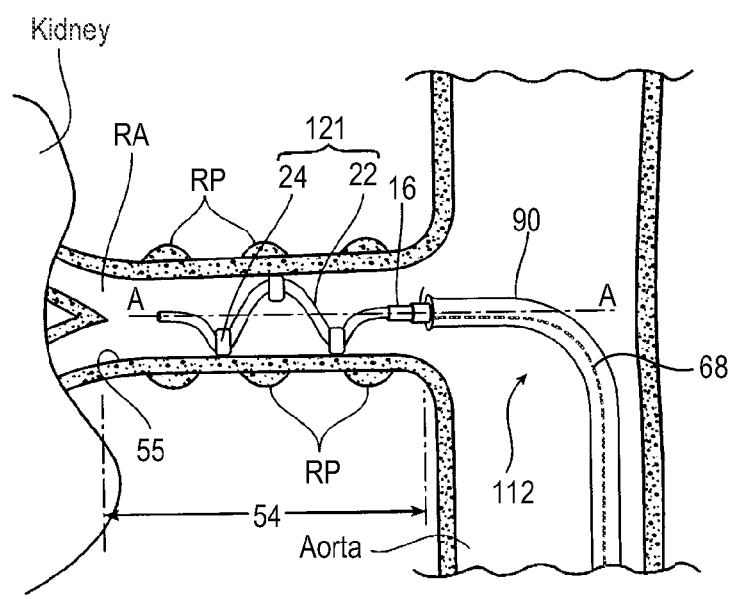
Figure 3C:
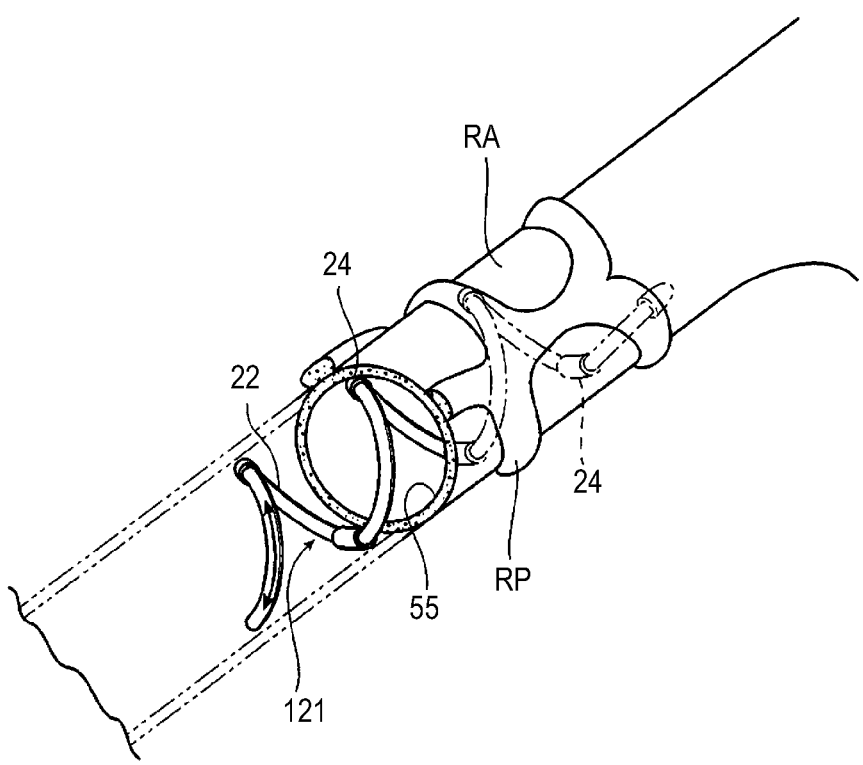

FIGS. 3A-3C provide an example of a treatment device 112 having a treatment or therapeutic assembly 121 configured to transform between a delivery state (FIG. 3A) and a deployed state (FIGS. 3B and 3C) within the renal artery RA. Referring first to FIG. 3A, a collapsed or delivery state of a therapeutic assembly 121 defines a low profile about the longitudinal axis A-A of the assembly such that a transverse dimension of the assembly is sufficiently small to define a clearance distance between an arterial wall 55 and the therapeutic assembly 121. The delivery state facilitates insertion and/or removal of the therapeutic assembly 121 and, if desired, repositioning of the assembly within the renal artery RA. As shown, the tuned control member 68 is coupled to a support structure 22 of the therapeutic assembly 121 (e.g., a flexible distal portion of the elongated shaft 16). In the delivery state, however, the tuned control member 68 is applying little or no tensile force to the structure because it is slack (e.g. not displaced).

In the collapsed configuration, the geometry of the therapeutic assembly 121 facilitates movement through a guide catheter 90 to the treatment site in the renal artery RA. Moreover, in the collapsed configuration, the therapeutic assembly 121 is sized and shaped to fit within the renal artery RA and has a diameter that is less than a renal artery inner diameter 52 and has a length (from a proximal end of the therapeutic assembly 121 to a distal end of the therapeutic assembly 121) that may be less than a renal artery length 54.

Referring to FIGS. 3B and 3C together, the therapeutic assembly 121 is shown in the deployed state (e.g., a generally helical/spiral arrangement). The tuned control member 68 is displaced (i.e., under tension) to apply a compressive force to the support structure 22, which transforms the therapeutic assembly 121 from its delivery state to its deployed state. As illustrated, the transformation of the therapeutic assembly 121 within the respective renal artery RA establishes apposition of energy delivery elements 24 against the tissue along the wall 55 of the respective renal artery RA for supplying treatment energy to target nerves via the respective energy delivery elements 24. In some embodiments or modalities, longitudinal or rotational manipulation of the therapeutic assembly 121 may also facilitate creating the desired contact sites between the energy delivery elements 24 and the wall 55 of the renal artery.

In the deployed state of this example, the support structure 22 of the therapeutic assembly 121 defines a substantially helical/spiral shape in contact with the arterial wall 55 along a helical/spiral path. One advantage of this arrangement is that pressure from the helical structure can be applied to a large range of radial directions without applying excessive pressure to a circumference of the vessel. Thus, the helically-shaped therapeutic assembly 121 is expected to provide stable contact between the energy delivery elements 24 and the arterial wall 55 when the wall moves in any direction. Furthermore, pressure applied to the arterial wall 55 along a helical path is less likely to stretch or distend a circumference of a vessel that could thereby cause injury to the vessel tissue. Still another feature of the expanded helical structure is that it may contact the arterial wall 55 in a large range of renal artery inner diameters 52 while leaving an unoccluded lumen in the vessel to allow blood to flow through the helix during therapy.

III. TUNED CONTROL MEMBERS

A conventional control wire can initiate transformation of a therapeutic assembly (e.g., the therapeutic assembly 21) when the control wire begins to be displaced, particularly by the proximal movement of the control wire proximal end. As displacement continues, the therapeutic assembly will transform (e.g., expand) until it is fully deployed. The displacement (or "throw" distance) for achieving appropriate deployment may depend on the tensile force needed to transform the therapeutic assembly. In general, progressive deployment of a therapeutic assembly requires corresponding proximal displacement of the control wire, and may or may not require increasing amounts of tensile force. That is, increasing deployment of a therapeutic assembly may be accomplished by continued displacement of a control wire 68 that may be applying a constant tensile load to first distal attachment location 56a. In other embodiments, increasing deployment of a therapeutic assembly may be accomplished by continued displacement of a control wire 68 that may be applying a corresponding increase in tensile load to first distal attachment location 56a.

The tensile force applied to first distal attachment location 56a in response to selective displacement of second attachment location 56b is dependent at least in part on the mechanical properties of the control wire material, particularly as depicted in the stress-strain curve for the control wire material. Conventional control wires are typically formed from metallic materials (or alloyed metallic materials) that can have different types of stress-strain responses. Some (ductile) materials exhibit mostly linear elastic regions of their stress-strain curves, while other materials, so-called superelastic materials, also have a subsequent portion of the stress-strain curve that plateaus corresponding to the formation of stress-induced martensite (SIM). That is, for a given range of strain, the stress in the superelastic material does not substantially increase in the plateau portion of the stress strain curve.

Figure 4A:
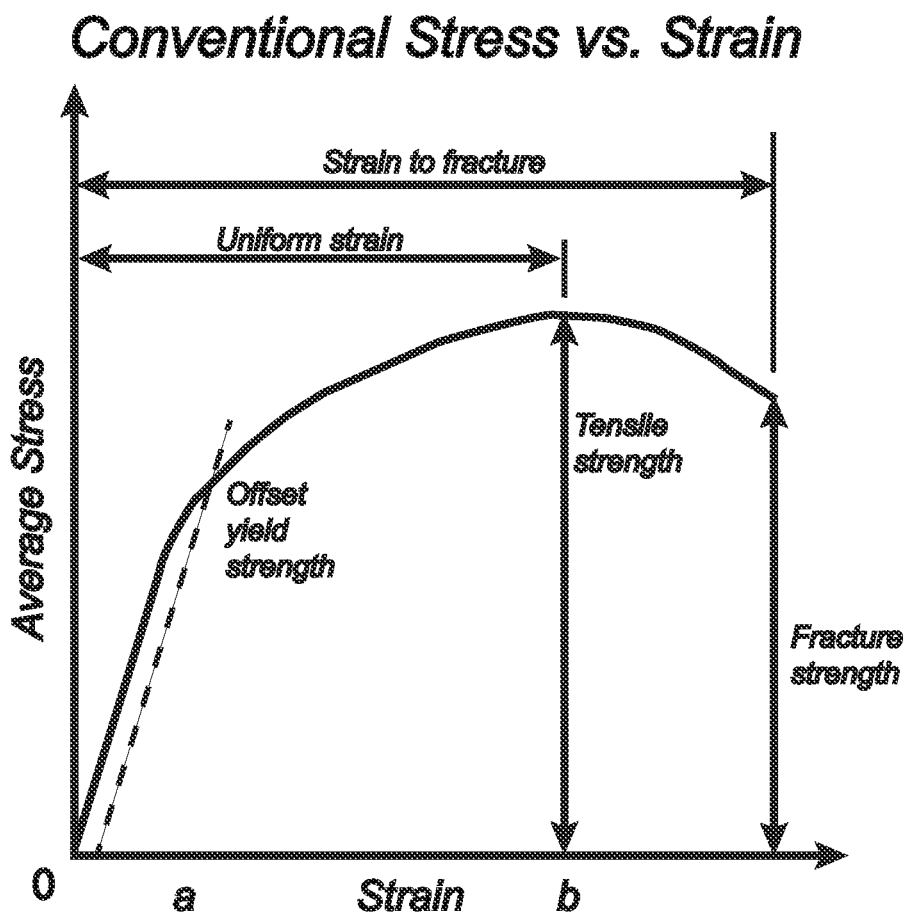
FIGS. 4A and 4B are respective diagrams of stress-strain responses for conventional or non-superelastic materials and for superelastic materials.
Figure 4B:
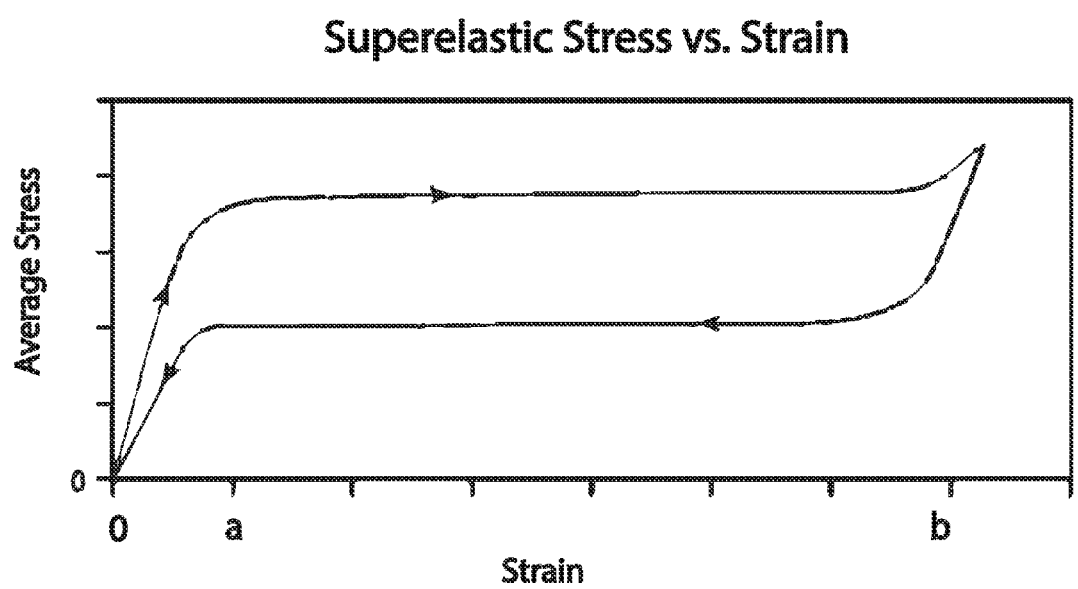

By way of example, FIG. 4A shows a diagram of a stress-strain curve for a typical non-superelastic metallic material. As strain across the material increases, the material becomes more stressed, with stress increasing linearly over a first elastic range (0 to a) of strain and non-linearly over a second plastic range (a to b) of strain. FIG. 4B shows a stress-strain curve of a typical superelastic material. Such material can include, for example, nitinol (nickel titanium binary alloy). As strain in the superelastic material increases, the material stress increases linearly over the first elastic range (0 to a). However, over a second superelastic range (a to b) the stress in the material plateaus before stress begins to increase again after the plateau region.

Known catheter control wires are made of superelastic material to enhance operation. For example, a superelastic control wire can be configured to operate in the plateau region of a stress-strain curve when strained beyond a certain length during operation. Thus, when an actuator displaces the proximal end of a superelastic control wire and, by pulling against resistance from the distal end of the catheter, applies sufficient linear deformation (i.e., strain) between distal attachment location 56a and proximal attachment location 56b to place the material in the stress plateau region of the stress-strain curve, displacement will increase but strain does not substantially increase.

Figure 5:
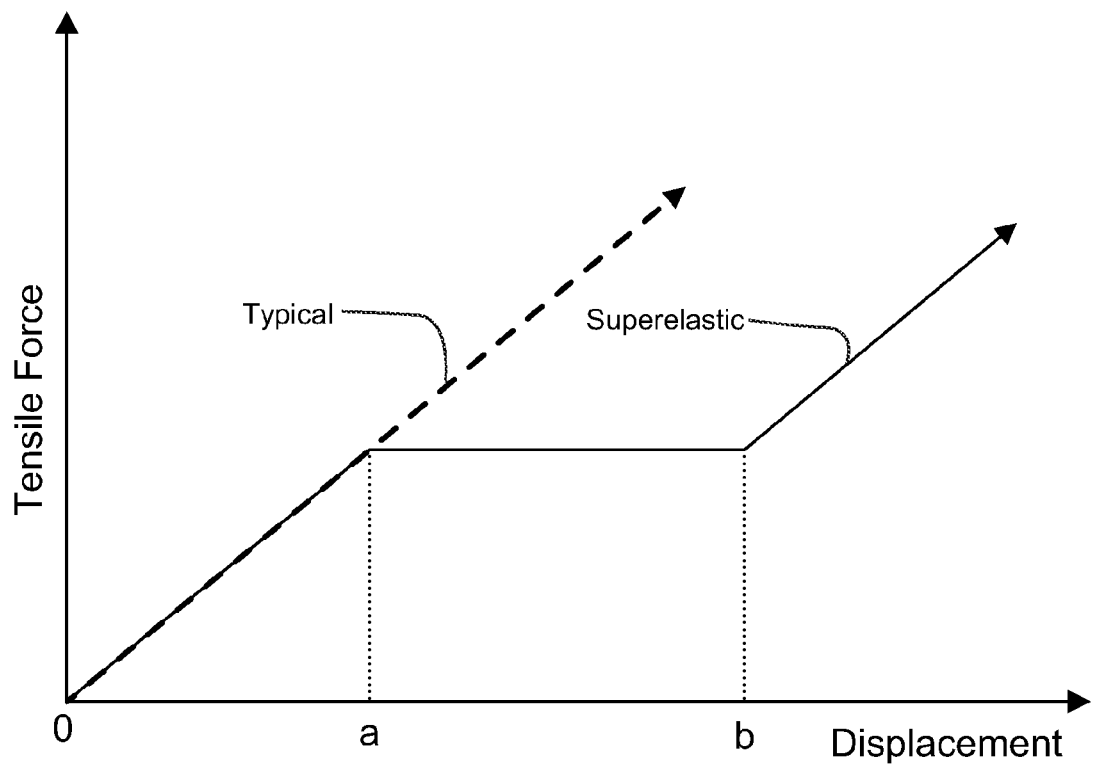
FIG. 5 is a diagram showing tensile force vs. displacement response of superelastic control wires and non-superelastic control wires.

FIG. 5 is a diagram showing a representative tensile force vs. displacement curve for a typical non-superelastic or ductile control wire material compared to that of a superelastic control wire. Over a first displacement range (0 to a) both control wires have a similar elastic response by linearly increasing tensile force in response to increasing displacement. However, over a second displacement range (a to b), the tensile force in the superelastic control wire plateaus (i.e. remains substantially constant), while the tensile force in the non-superelastic control wire continues to increase.

As illustrated by FIG. 5 (and with reference to FIGS. 3A-3C), material choice (e.g., a superelastic material over a non-superplastic material) can provide some design control of the tensile force-displacement relationship for a catheter control wire. However, a given length and diameter of nitinol control wire may only be able to provide one type of force vs. displacement response. The intended deployment of the therapeutic assembly 121 may require a force vs. displacement response that cannot be provided by a conventional nitinol control wire. For example, deploying therapeutic assembly 121 as designed may require a shorter nitinol control wire to achieve a targeted amount of deployment force with less displacement or throw of actuator 36. Such a nitinol control wire may be too short to extend fully between distal attachment location 56a and proximal attachment location 56b. Alternatively, deploying therapeutic assembly 121 as designed may require a thicker nitinol control wire to achieve a targeted amount of deployment force with less displacement or throw of actuator 36. Such a thicker nitinol control wire may be too stiff to permit flexible navigation of tortuous vascular anatomy with treatment device 12.

Embodiments of the present technology, however, provide a control member that can be configured for use in a variety of applications where it might not be possible, practical, or otherwise desirable to use either a conventional ductile control wire or a superelastic control wire. In particular, the tuned control member 168 can provide a customized force vs. displacement response. For example, in some applications, it is desirable to have an elongate treatment device (e.g., the treatment device 12) that can be configured with a specific amount (or range) of displacement (or throw) by actuator 36 to achieve deployment of the therapeutic assembly 121. In other applications, it is desirable to operate the tuned control member 168 in a displacement regime where the treatment assembly is not fully deployed. For example when an expandable treatment assembly (e.g., the therapeutic assembly 121) is delivered to a small diameter artery (within the range of artery sizes treatable with the treatment assembly), attempting to fully expand the treatment assembly beyond the diameter of the artery lumen could create excessive forces against the arterial wall. Treatment assemblies including control members configured in accordance with embodiments of the present technology are expected to address such issues.

Figure 6A:
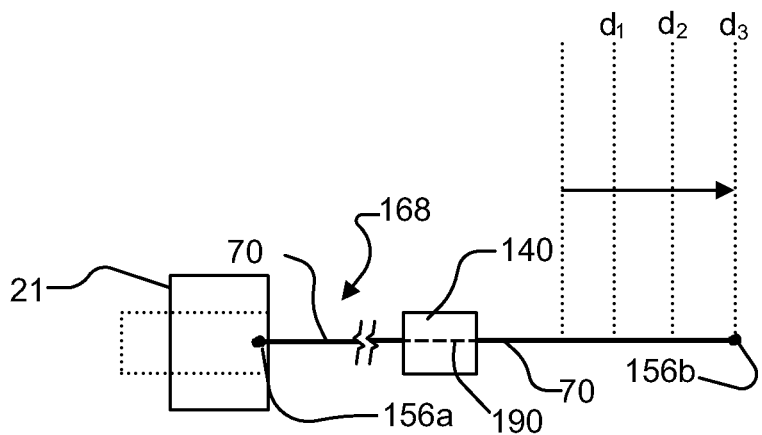
FIG. 6A is a schematic diagram illustrating a tuned control member and operation of a tuned control member over different ranges of displacement in accordance with an embodiment of the present technology.
Figure 6B:
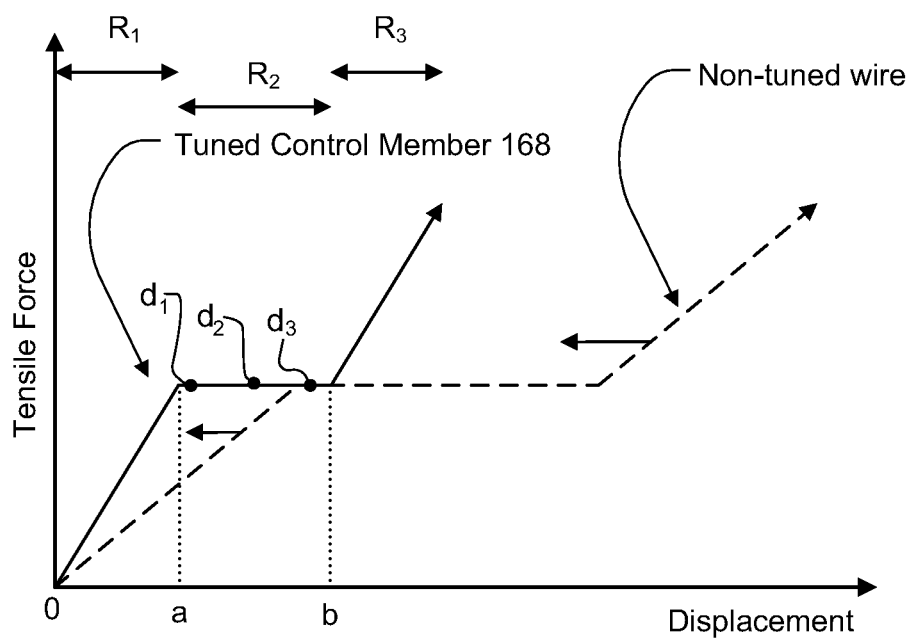
FIG. 6B is a graph representing tensile force response over the different ranges of displacement of FIG. 6A.

FIG. 6A, for example, is a schematic diagram illustrating a tuned control member 168 and operation thereof over different ranges of displacement in accordance with an embodiment of the present technology. FIG. 6B is a graph representing tensile force (stress) response over the different ranges of displacement for the tuned control member 168 of FIG. 6A and a non-tuned superelastic control wire. As used herein, the term "tensile force" generally refers to the component of force created in response to strain (see, e.g., FIGS. 4A and 4B). A person of ordinary skill in the art will appreciate that the tensile force in a given application can be based on other components of force. For example, some components of tensile force are attributable to frictional forces within the shaft 16 (FIG. 1).

Referring to FIGS. 6A and 6B together, the tuned control member 168 includes the wire 70 and at least one tuning component 140 (shown schematically in this example) operably coupled to the wire 70 at one end thereof or located between the ends of wire 70, as illustrated. In the illustrated embodiment, the wire 70 includes a superelastic material (e.g., nitinol); however, in other embodiments, the wire 70 may comprise non-superelastic, e.g., ductile material. The tuned control member 168 is operably coupled between a first attachment location 156a and a second attachment location 156b. The first attachment location 156a can be located, for example, at or near the therapeutic assembly 21, and the second attachment location 156b can be located, for example, at or near the actuator 36 (FIG. 1). In some embodiments, multiple tuning components can be distributed at two or more locations along the tuned control member 168.

In operation, the tuned control member 168 is configured to achieve a desired tuned force-displacement response. In particular, the tuning component 140 modifies the stress-strain response that a non-tuned control wire would ordinarily provide without the intervening tuning component 140. Referring to the graph of FIG. 6B, the tuned control member 168 and the conventional control wire both have superelastic responses, i.e., plateaus in their respective force/displacement curves. However, the plateau in the force/displacement curve of the tuned control member 168 begins at a smaller displacement (a) than the plateau in the force/displacement curve of the non-tuned control wire. The tuned control member 168 provides a generally linear, elastic force response over a first displacement (strain) range $R_1$ (displacement 0 to displacement a), a generally constant force response over a second displacement range $R_2$ (displacement a to displacement b), and again a generally linear force response over a third displacement range $R_3$ (displacement b to displacement c). For purposes of comparison, the non-tuned control wire is assumed to have the same properties (e.g., same diameter, same material, etc.) as wire 70 of the tuned control member 168. Also, the slopes, shapes, and other features of the plot in the graph provide one example of the operating behavior (i.e., tuned displacement) of the tuned control member 168. A person of ordinary skill in the art will appreciate, however, that the actual force/displacement response can depend on the particular physical configuration and mechanical properties of the tuned control member. For example, the force represented by the plateau region of the force/displacement response curve can be higher or lower and can begin at a greater or lesser displacement (a), as selected by the designer.

Referring to FIGS. 6A and 6B together, when the tuned control member 168 is strained by a first displacement distance $d_1$ within the first range $R_1$, the resulting tensile force causes the therapeutic assembly 21 to at least partially deploy. As displacement of the tuned control member 168 increases over the first displacement range $R_1$, the tensile force applied at attachment location 156a increases in a linear relationship. When displacement reaches the first displacement (a), the therapeutic assembly 21 will be at its fully deployed or expanded state. By contrast, by the end of the first displacement (a), the non-tuned control wire has yet to reach the plateau region.

As discussed above, in some applications only a relatively small amount of control member displacement is desired to appropriately deploy a treatment assembly. Thus, in such embodiments, the tuned control member 168 provides an advantage over many conventional control wires in that the linear response in the first range $R_1$ is more steep than the linear response of the non-tuned control wire. This is expected to allow a desired tensile force to be achieved with a smaller amount of displacement as compared to non-tuned control wires without increasing the thickness or diameter of wire 70, which could disadvantageously increase stiffness in the distal region of the assembly.

When the tuned control member 168 is displaced over the second range $R_2$, the force applied at attachment location 156a remains nearly constant. For example, a second displacement distance $d_2$ and a third displacement distance $d_3$ apply generally the same tensile force at the therapeutic assembly 21. Thus, the constant tensile force applied at attachment location 156a anywhere in displacement range $R_2$ can maintain the deployed state of the therapeutic assembly 21, with little sensitivity to the displacement applied at attachment location 156b (e.g., by actuator 36).

When the tuned control member 168 is in the third displacement range $R_3$, it linearly increases the tensile force applied to the therapeutic assembly 21. In some embodiments, operation in this range may be less preferable because it may create excessive pressure on a wall of the anatomical vessel, lumen, renal artery, etc. Operation in this range may also be less preferable because it may create potential damage to the tuned control member 168, the tuning component 140, and/or the therapeutic assembly 21. In some embodiments, an increase in tensile force prior to a breaking event may indicate to a clinician that the tuned control member 168 is in the third displacement range $R_3$. That is, a clinician may be able to sense an increase in tensile force at actuator 36 when control member 168 is transitioning from the second displacement range $R_2$ to the third displacement range $R_3$. This indication can prevent the clinician from imparting too much force to the support structure 22 (FIG. 3B). In such a scenario, the clinician can reduce the amount of tensile force such that the tuned control member 168 returns to at least the second displacement range $R_2$. Thus, in one embodiment of a catheter 12 incorporating a tuned control member 168, operation of actuator 36 may quickly (e.g., with a short throw) achieve deployment of therapeutic assembly 21 in a variety of vessel lumen sizes while providing a safety margin (e.g., a constant force) against applying too much expansion force and without requiring an overly stiff control wire in a distal region of the catheter.

According to various embodiments of the present technology, a tuned control member can be manufactured to have a desired tuned displacement. For example, the longitudinal stress-strain relationship of the tuned control member 168 can be determined with a conventional tensometer by gripping the member at its ends, then stretching the member and measuring the amount of longitudinal deformation (strain) at defined intervals and the corresponding tensile load (stress). The tuning component 140 and/or the wire 70 can be selected and/or configured based on this type measurement.

Figure 7A:
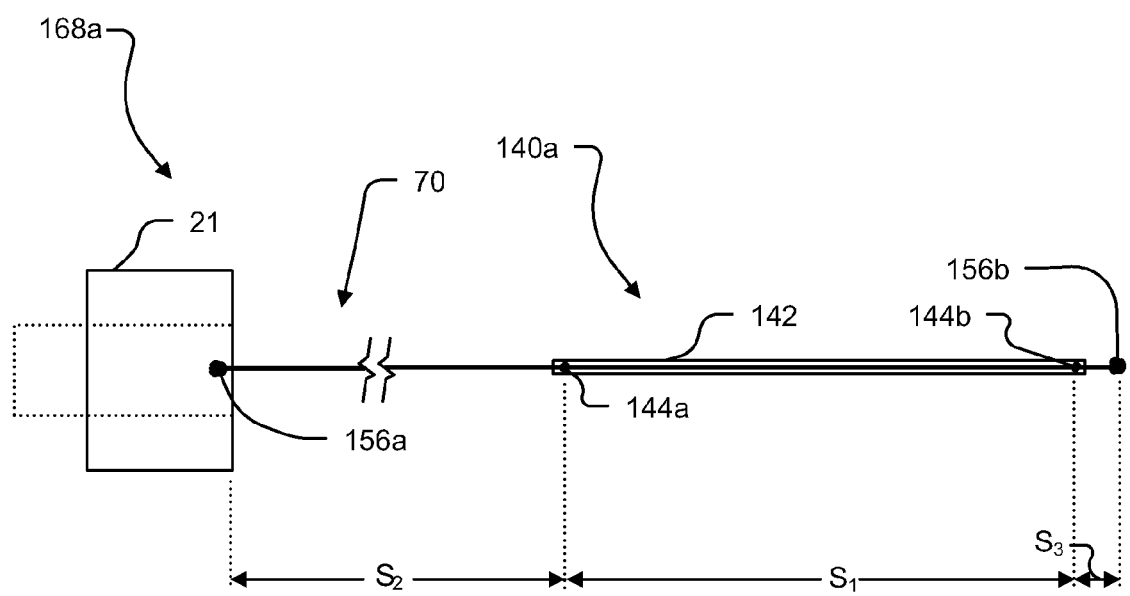
FIGS. 7A-7D illustrate various tuned control members configured in accordance with embodiments of the present technology.

FIGS. 7A-7D illustrate various tuned control members configured in accordance with embodiments of the present technology. For purposes of clarity, the handle 34 and shaft 16 are not shown. FIG. 7A, for example, is a schematic view of a tuned control member 168a and a tube-based tuning component 140a. The tube-based tuning component 140a includes a tubular member ("tube 142") through which wire 70 extends. The wire 70 can be coupled to the tube 142 at anchoring locations 144 (identified individually as first and second anchoring locations 144a and 144b) via adhesive, epoxy, fusing, mechanical locking, solder (e.g., nitinol solder), or other suitable anchoring techniques. In some non-illustrated embodiments, the tube 142 may be directly attached to the second attachment location 156b, for example, at or near the actuator 36 (FIG. 1). As such, the second anchoring location 144b at the tube 142 can be omitted in these embodiments and wire 70 may be inserted within the tube 142 only far enough to be attached at anchoring location 144a. In other embodiments, the tube 142 can include more than two anchoring locations 144 or an anchoring material (e.g., epoxy) at least partially filling a gap within the tube 142 between the wire 70 and the tube 142. In addition or alternatively, the tuning component 140a can include more than one tube 142 positioned along wire 70.

The tube 142 may have an elasticity that is different than the elasticity of the wire 70 and can be selected to achieve a desired tuned displacement. For example, in one particular embodiment, the tube 142 can be constructed from a material such as stainless steel or other material that is relatively stiffer than wire 70. In addition, the spacing $S_1$ between the first and second anchoring locations 144a and 144b can be selected relative to spacings $S_2$ and $S_3$ outside the first and second anchoring locations 144a and 144b. A desired ratio of the spacings (e.g., $S_1/(S_2+S_3)$) can provide a desired ratio of elasticity between the elasticity of the tube 142 between the anchoring locations 144a and 144b and the elasticity of wire 70 outside these locations.

In general, in embodiments where the stiffness of tube 142 is greater than the stiffness of the wire 70, an increase in the spacing S1 between the first and second anchoring locations 144a and 144b tunes the control member 168a such that less displacement is required to achieve a suitable deployment force (e.g., a steeper slope in range R1 of the force/displacement curve.). As the spacing S1 increases, the stress-strain behavior of the tuned control member 168a can be based in larger part on the force/displacement response of the tube 142 between the first and second anchoring locations 144a and 144b. On the other hand, a decrease in the spacing S1 between the first and second anchoring locations 144a and 144b can increase the amount of displacement necessary for achieving suitable deployment. The distal portion of wire 70 between attachment locations 144a and 156a can be more flexible than tube 142, such that, in some embodiments, the distal portion of wire 70 can permit the composite assembly including the portion of catheter 12 surrounding the distal portion of wire 70 to flexibly navigate tortuous portions of vasculature.

In other non-illustrated embodiments, the tuning component 140a may comprise a wire. For example, the tuned control member 168a can include a first wire 70 and the tuning component 140a can include a second wire that is coupled to the first wire 70, such as by bonding, tying, or knotting the first and second wires. The first wire 70 and the second wire can have different stress/strain behavior, with the ratios of their respective stress-strain behavior selected by the material choice and/or diameter or length of the first and second wires. In some embodiments, the ratio of the length of the first wire to the length of the second wire can be selected to provide a desired tensile force vs. displacement response profile.

Figure 7B:
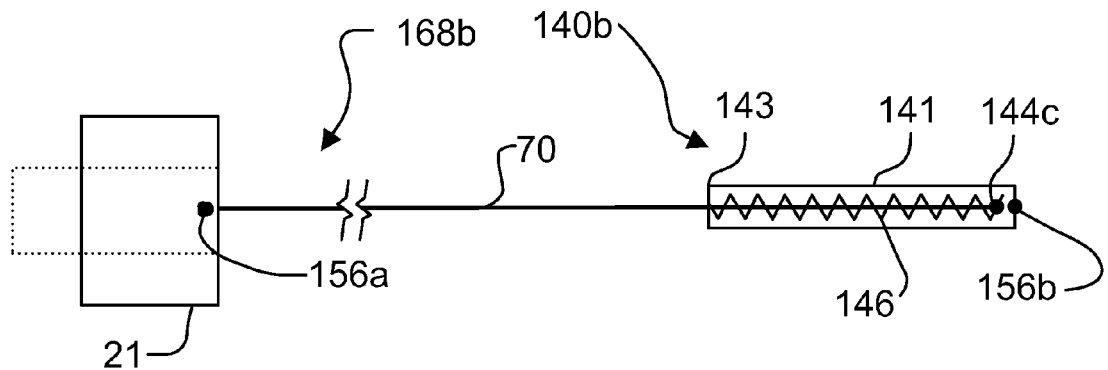

FIG. 7B is a schematic view of the therapeutic assembly 21 and a tuned control member 168b operably coupled to the therapeutic assembly 21 in accordance with another embodiment of the technology. In this embodiment, the tuned control member 168b comprises a spring-based tuning component 140b including at least one spring element 146 (e.g., a coiled compression spring). Similar to the tuning component 140a described above with reference to FIG. 7A, the tuned control member 168b is configured to achieve a desired tuned force-displacement response by modifying the stress-strain response that a non-tuned control wire would ordinarily provide. For example, a spring constant and/or a length of the spring element 146 can be selected by a designer to provide a desired force-displacement response for the tuned control member 168b.

In the illustrated embodiment, the spring-based tuning component 140b comprises a sleeve 141 housing the spring element 146 and the wire 70. The proximal portion of wire 70 extends through the inner diameter of spring 146 and the proximal end of wire 70 is attached to the proximal end of spring 146 at location 144c. The distal end 143 of sleeve 141 is open to receive wire 70 and is attached to or provides a seat for spring 146. In this embodiment, second attachment location 156b provides, for example, a connection between the proximal end of sleeve 141 and actuator 36. When tuned control member 168b is placed under tension between attachment locations 156a and 156b, sleeve 141 applies compression load to spring 146 at sleeve end 143. Sleeve 141 can help keep spring 146 from buckling under such loads. The proximal end of spring 146 transfers the load to the proximal end of wire 70 and location 144c.

The tuning component 140b can be located at any of a variety of locations on the treatment device 12 (FIG. 1). For example, the tuning component 140b can be positioned within the handle 34 (FIG. 1) and/or the shaft 16 (FIG. 1). In some embodiments, the tuning component 140b can include a knob, set screw, or other feature for setting/adjusting the axial length of the spring element 146 that, in turn, may change the behavior of the tuning component 140b.

Figure 7C:
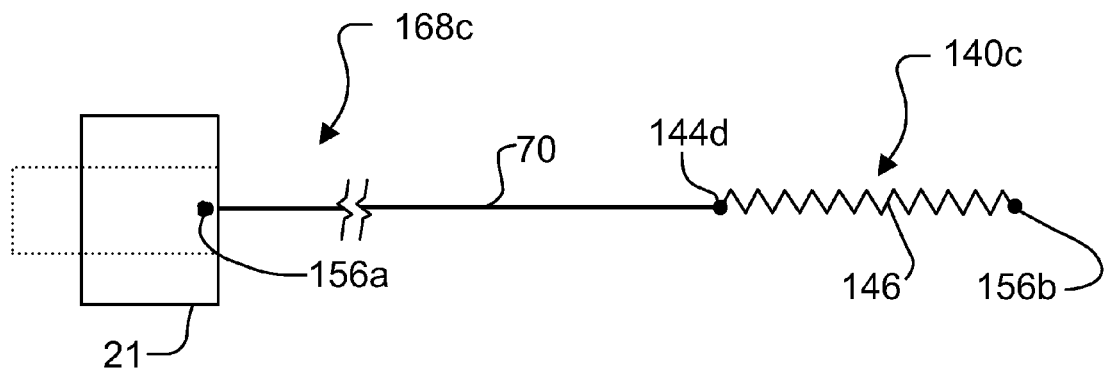

FIG. 7C is a schematic view of the therapeutic assembly 21 and a tuned control member 168c operably coupled to the therapeutic assembly 21 in accordance with another embodiment of the technology. Similar to the tuning component 140b described above with reference to FIG. 7B, the tuned control member 168c comprises a spring-based tuning component 140c including at least one spring element 146 (e.g., a coiled tension spring).

In the illustrated embodiment, the spring-based tuning component 140c comprises a spring element 146 attached to the proximal end of wire 70 at location 144d. In this embodiment, second attachment location 156b provides, for example, a connection between the proximal end of spring 146 and actuator 36. When tuned control member 168c is placed under tension between attachment locations 156a and 156b, the distal end of spring 146 transfers the load to the proximal end of wire 70 at location 144d. Thus, in this embodiment, the tensile force vs. displacement response profile for tuned control member 168c is the sum of the tensile force vs. displacement properties of wire 70 and spring 146, which are mechanically joined in series.

Figure 7D:
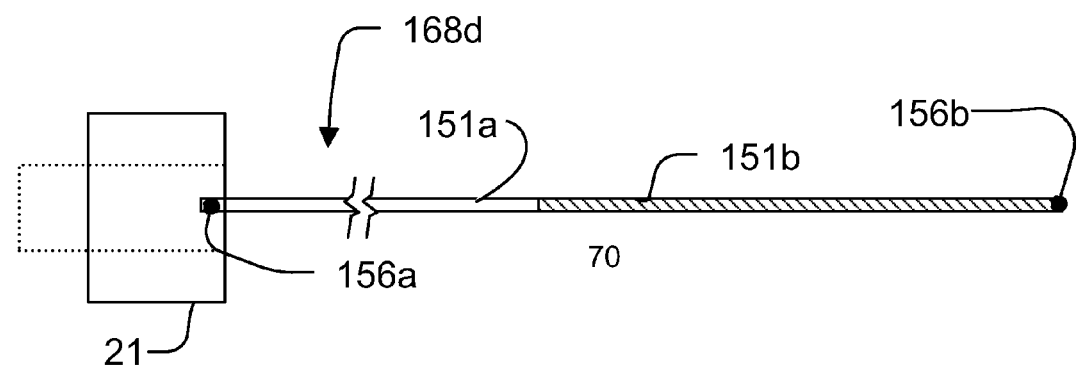

In further embodiments, tuning can be achieved by chemically, thermally, and/or mechanically treating a portion of the wire 70. FIG. 7D, for example, is a schematic view of a tuned control member 168d having the wire 70 with a first portion 151a and a second portion 151b. One or more of the portions 151a-b may be treated using various techniques (e.g., heat treatment, cold working, chemical treatment). In one embodiment, for example, the tuned control member 168d can include a nitinol wire 70 that is heat treated or cold worked such that the treated portion is relatively stiffer than an untreated portion. In another embodiment, a wire 70 can be trimmed, tapered, or otherwise thinned at the first portion 151a. In various embodiments, the portions can also be selected to achieve a desired ratio of stress-strain responses. For example, and similar to the tube 142 of FIG. 7A, the relative lengths of the portions 151 can tune the stress-strain response of the tuned control member 168c.

IV. TREATMENT DEVICES

FIGS. 8-13D illustrate treatment devices and related components configured in accordance with embodiments of the present technology. In several embodiments, these treatment devices and components can be utilized with treatment assemblies that are configured to expand in transverse dimension (e.g., helically/spirally expand) from a delivery state to a deployed state. As such, many are described below with reference to the therapeutic assembly 121 (FIGS. 3A-3C). In other embodiments, other types of treatment devices can include the various features of these embodiments. Further, in several embodiments, the following treatment devices, components, and related embodiments thereof work in combination with the tuned control member 168 (FIGS. 6A and 6B). Thus, many of these embodiments, are also described below with reference to the tuned control member 168. However, in other embodiments, certain aspects may work in combination with a non-tuned control member.

Figure 8:
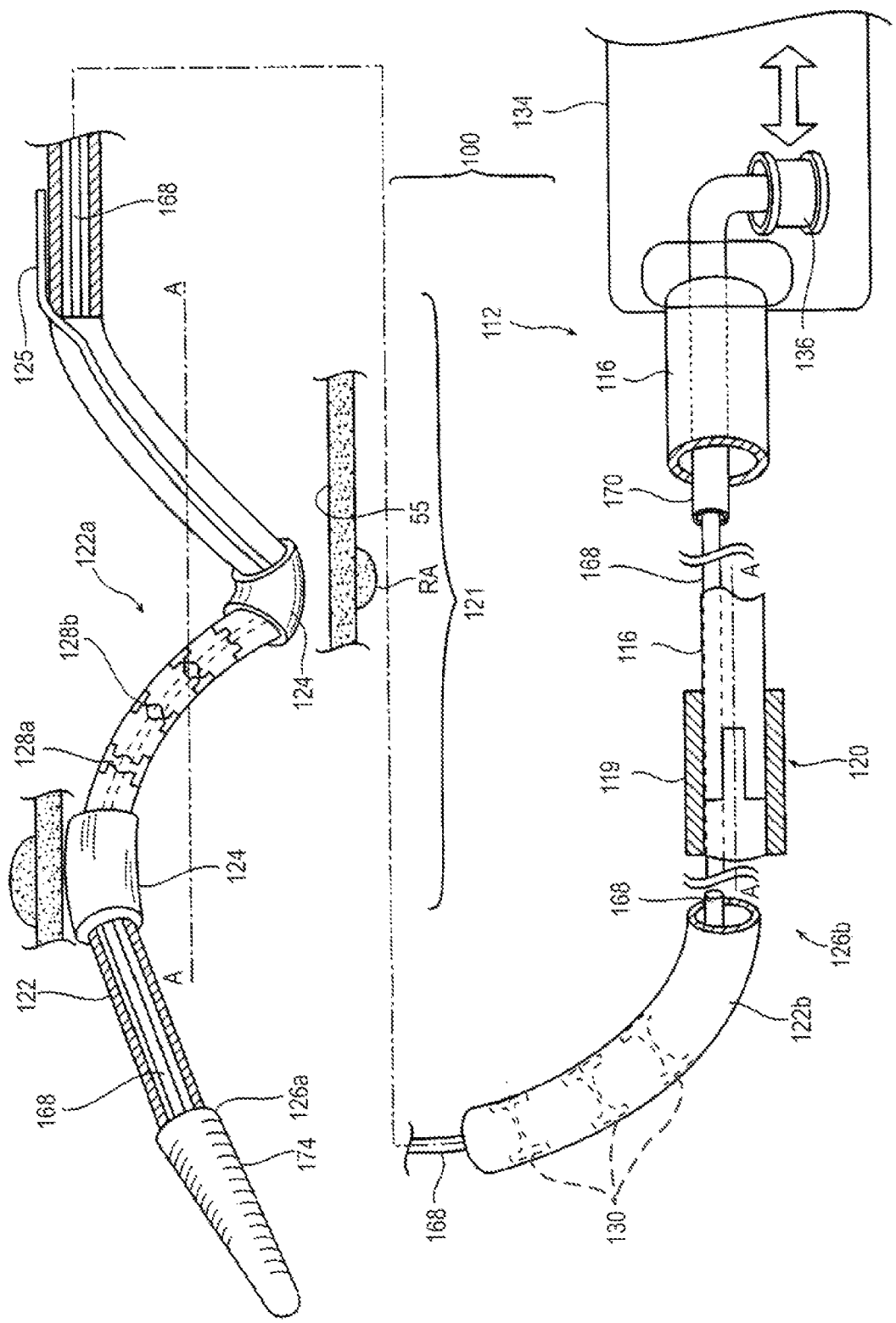
FIG. 8 is a broken perspective view in partial section of a treatment device configured in accordance with an embodiment of the technology.

FIG. 8, for example, is a broken perspective view in partial section of a treatment device 112 in which embodiments of the tuned control member 168 may be incorporated. The treatment device 112 can include a catheter having an elongated shaft 116 with a distal region 126a for delivery and deployment of a therapeutic assembly 121 (e.g., a treatment section) at a target treatment site in a lumen and, in particular, for performing renal neuromodulation within a renal blood vessel (e.g., a renal artery). Disposed at a proximal end of the elongated shaft 116 is a handle assembly 134 (shown schematically) for manipulation of the elongated shaft 116 and the therapeutic assembly 121. More specifically, the handle 134 is configured to provide for remote operation of the tuned control member 168 for controlling or transforming the therapeutic assembly 121 between a delivery state and a deployed state. In particular, the handle 134 is configured with an actuator 136 (schematically shown) to provide for remote operation of the tuned control member 168.

The treatment device 112 is configured to deliver the therapeutic assembly 121 to the treatment site in a delivery state (not shown) in which the therapeutic assembly 121 is substantially linear (e.g., straight) such that energy delivery elements 124 are substantially axially aligned along a support structure 122. Energy supply wires 125 may be disposed along an outer surface of the support structure 122 and coupled to each of the energy delivery elements 124 for supplying treatment energy to the respective energy delivery elements 124. Once located at the treatment site within the renal artery, actuation of the tuned control member 168 transforms the therapeutic assembly 121 from the delivery state to the deployed state as shown. In the illustrated embodiment, the tuned control member 168 is disposed within a tubular portion 123 of the support structure 122. One end of the tuned control member 168 may be affixed at or near a distal region 126a of the support structure 122 (e.g., terminating in a distal tip 174). The opposite end of the tuned control member 168 can terminate within the handle 134 and be operably coupled to an actuator (e.g., the actuator 136) for transforming the therapeutic assembly 121 between the delivery and the deployed state.

The tension in the tuned control member 168 can provide a proximal and/or axially directed force to the distal region 126a of the support structure 122. For example, under the influence of the tension force in the tuned control member 168, the distal region 126a of the support structure 122 is configured to deflect. A distal deflection region 122a can include a plurality of slots 128 (only two are labeled as 128'a and 128'b). The slots 128'a and 128'b formed in the distal deflection region 122a of the support structure are positioned to bias the deflection of the distal region 126a so as to form one or more curved portions, each having a radius of curvature preferably defined by the number of deflection slots 128, the individual slot width, slot configuration, and/or slot arrangement. As the distal region 126a continues to deflect, it radially expands to place one or more of the energy delivery elements 124 (now spaced apart) into apposition with the wall 55 of the renal artery RA. The support structure 122, when subject to the tension of the tuned control member 168 and the radial constraints of the wall 55, is configured to form a substantially helical shape so as to axially space and radially offset the energy delivery elements 124 from one another. Moreover, because the distal deflection region 122a of the support structure 122 is configured to form a helical geometry within the renal artery RA when under a tension load, the therapeutic assembly 121 is not expected to radially overload the wall 55 of the renal artery RA. Rather, the support structure 122 deforms to form the helix under a continuously increasing tension load. In one particular embodiment, an amount of tension to fully deploy the treatment device 112 is typically less than, for example, about 0.68 kgF (1.5 lbf pound-force) applied at the distal region 126a of the therapeutic assembly 121, e.g., between about 0.45 kgF (1 lbf) to about 0.68 kgF (1.5 lbf)).

The support structure 122 of the therapeutic assembly 121 can further include a proximal region 126b that defines an orientation region 122b of the assembly for locating the therapeutic assembly adjacent to the wall 55 of the renal artery RA. As shown in FIG. 8, the proximal region of the support structure 122 includes a plurality of orientation slots 130'. In operation, upon actuation of the handle 136 to place the tuned control member 168 under tension, the orientation region 122b deflects in a radially outward direction within the renal artery RA to locate the therapeutic assembly 121 into contact with the wall 55. More specifically, the slots 130' deform under the tension force so as to deflect the orientation region 122b radially outward from the longitudinal axis A-A of the support structure 122

The tuned control member 168 can be comprised of ultra-high molecular weight polyethylene (UHMWPE) fiber such as, for example, high strength, gel-spun fiber sold under the trademark SPECTRA or other sufficiently strong polyethylene fiber. Alternatively, nitinol or other mono- or multi-filament types can be used provided they are compatible with the application and can transmit the appropriate tensile force to the therapeutic assembly 121. In one particular embodiment, for example, the tuned control member 168 can be comprised of nitinol and a diameter of 0.15 mm (0.006 inch). In other embodiments, however, the tuned control member 168 may be composed of different materials and/or have a different diameter.

Figure 9A:
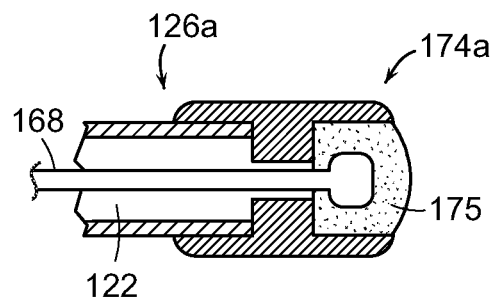
FIGS. 9A-9D illustrate various configurations of tip attachment at the distal portion of a support structure configured in accordance with embodiments of the present technology.
Figure 9B:
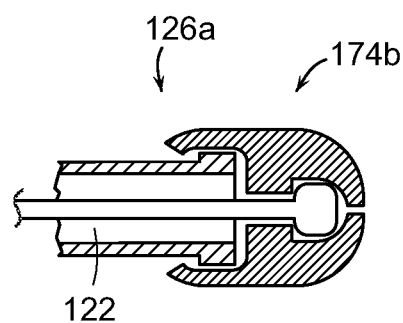
Figure 9C:
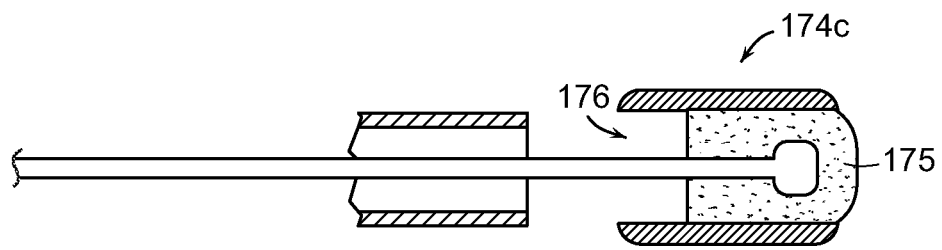
Figure 9D:
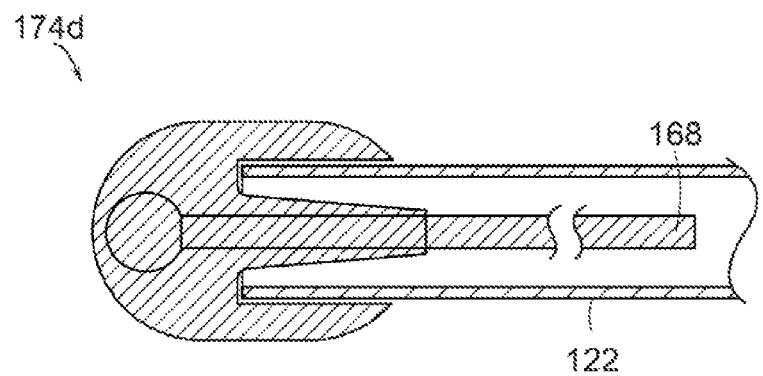

FIGS. 9A-9D, for example, illustrate various anchoring configurations for attachment of the tuned control member 168 at the distal region 126a of the support structure 122. As shown in FIG. 9A, a spherical distal tip 174a can be shaped to hold the tuned control member 168 with solder or adhesive 175 that secures the spherical distal tip 174a to the distal region 126a of the support structure 122. FIG. 9B illustrates another configuration in which a crimpable distal tip 174b is crimped at the distal region 126a of the support structure 122. In another embodiment shown in FIG. 9C, a distal tip 174c can be shaped to have a lumen therethrough ("thru lumen 176"), and solder or adhesive 175 can hold the distal tip 174c in place within the thru lumen 176. FIG. 9D shows a cross sectional view of a polymer tip 174d mounted to the support structure 122 and the tuned control member 168. The polymer tip 174d can be shaped as an over-molded head that is formed over the spherical end of the tuned control member 168. The head of the polymer tip 174d can be shaped such that deflector can be pressed into the head of the tip. In still other embodiments, the tip may have a different arrangement and/or include different features.

Referring back to FIG. 8, in some embodiments radiopaque materials may be located at the support structure 122 to aid in a clinician's manipulation of the treatment device 112 and to determine if the therapeutic assembly 121 is appropriately placed and/or deployed in the renal artery RA. Such radiopaque materials, for example, are capable of being imaged fluoroscopically and can include materials such as barium sulfate, bismuth trioxide, bismuth subcarbonate, powdered tungsten, powdered tantalum, or various formulations of certain metals, including gold, platinum, and platinum-iridium. These materials can be directly incorporated into the support structure 122 or may form a partial or complete coating of the support structure 122. Additionally or alternatively, radiopaque materials can be incorporated into the distal tip 174.

Under some operating conditions, the support structure 122 may not be delivered to a position extending far enough beyond a distal end of the guide catheter. In some cases, when the support structure 122 is expanded in this scenario, the most proximal electrode of the energy delivery elements 124 may be positioned too close to the distal tip of the guide catheter, thus preventing the support structure 122 from expanding to its full diameter. As a result, when the catheter is rotated to create a desired lesion between the most proximal electrode (e.g., the electrode 124a shown in FIG. 8) may not make sufficient contact with the vessel (e.g., for the full 360 degree rotation). The placement of radiopaque materials as described herein can be employed for fluoroscopic detection of placement.

Figure 10:
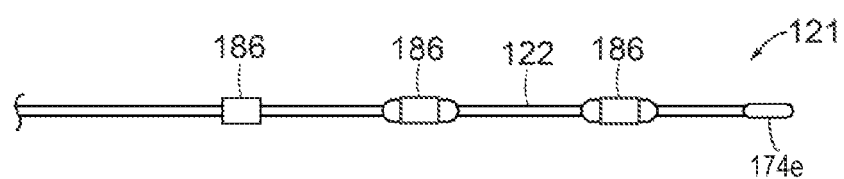
FIG. 10 illustrates marker bands that can be located at a support structure for detecting placement of the support structure within a patient's anatomy in accordance with an embodiment of the present technology.

In some embodiments, one or more radiopaque marker bands can be positioned at the support structure 122. For example, as shown in FIG. 10, one or more marker bands 186 may be mounted or otherwise placed around the support structure 122 (shown schematically) at proximal, distal, and/or intermediary locations therebetween along the support structure 122. The individual marker bands 186 can be secured to the support structure 122 using a variety of suitable techniques (e.g., adhesive, detents, etc.) such that the markers are securely held in place during operation. The marker band location at the support structure 122, for example, may be selected to indicate to a clinician that the support structure 122 has been properly deployed at the desired target location. In some embodiments, a clinician can detect the relative spacing difference between two or more marker bands 186 (or between at least one marker band 186 and the (radiopaque) distal tip 174 (not shown)) when in the deployed (expanded) state compared to the delivery state. The marker band location can additionally or alternatively be based on the location of a marker band with respect to the location of the distal end of the guide catheter.

Figure 11E:
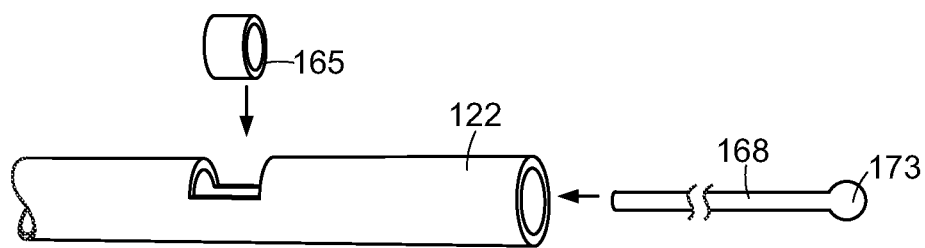

FIGS. 11A-11J illustrate various anchoring configurations for the tuned control member 168 at a location between the distal region 126a and the proximal region 126b of the support structure 122. For example, referring to FIGS. 11A and 11B together, the tuned control member 168 can be routed through a first opening or hole 160a in the support structure 122. A control wire tip 173 can be held in place by a pin 162 that is press fit into a second opening or hole 160b in the support structure 122. As best seen in FIG. 11B, for example, the pin 162 is configured to hold the control wire tip 173 within an interior region of the support structure 122 after the tuned control member 168 has been pulled through the first opening 160a. An adhesive 164 (FIG. 11B), such as biocompatible adhesive or epoxy, can at least partially fill or seal the first opening 160a. In some embodiments, the pin 162 may be configured to extend through the second opening 160b and another hole or opening in the support structure 122 opposite the second opening 160b (not shown). In still further embodiments, the pin 162 may have other features and/or a different arrangement.

FIGS. 11C and 11D illustrate another anchoring configuration in accordance with an embodiment of the present technology. In this configuration, a wire stop 163 may be employed to anchor the tuned control member 168. Rather than installing the tuned control member 168 through the first opening 160a (FIG. 11A), the tuned control member 168 can be routed through a third opening or hole 160c at the distal deflection region 122a of the support structure 122, with the wire stop 163 and the adhesive 164 holding the tuned control member 168 in place.

Figure 11F:
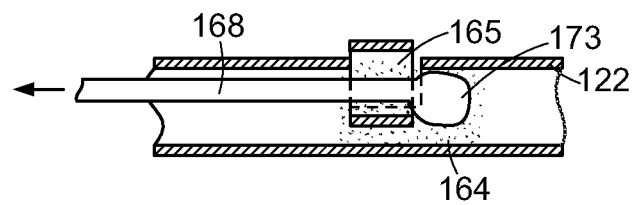
Figure 11G:
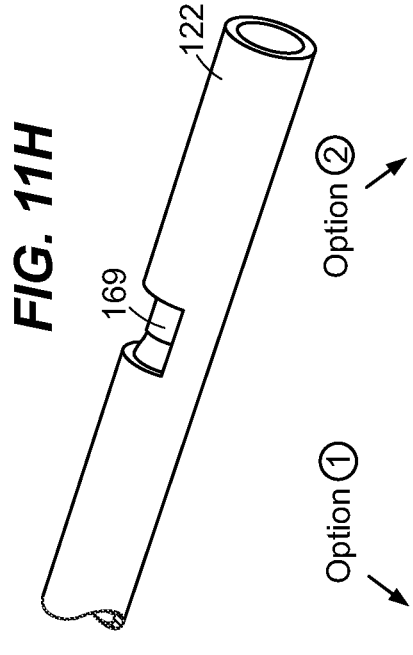

FIGS. 11E and 11F illustrate yet another anchoring configuration in accordance with an embodiment of the present technology. Referring to FIGS. 11E and 11F together, an anchor ring 165 is shown positioned in a slot 166 of the support structure 122. The anchor ring 165 is arranged to hold the control wire tip 173 in place via the adhesive 164. FIGS.

Figure 11H:
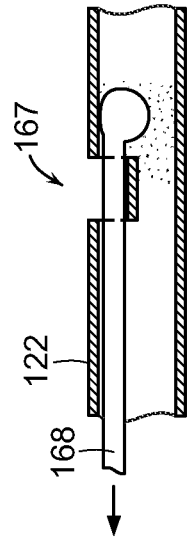
Figure 11I:
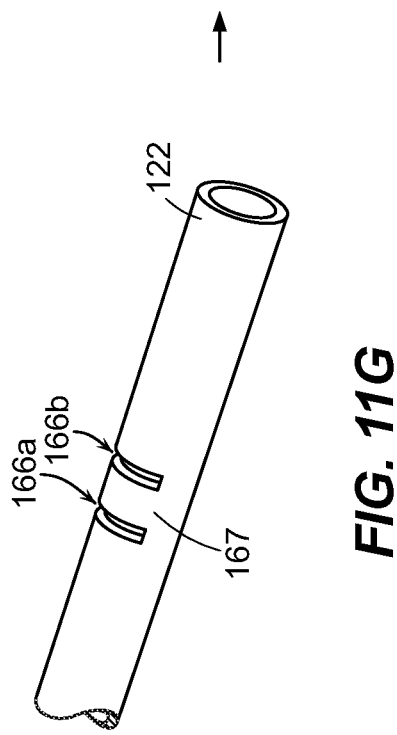
Figure 11J:
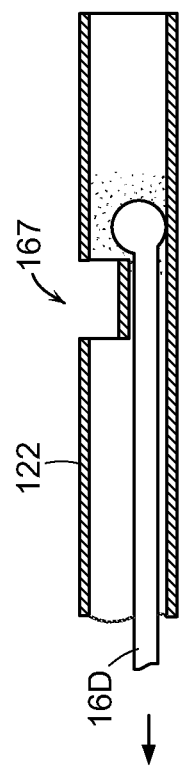

11G-11J illustrate another anchoring arrangement having first and second machined slots 166a and 166b that define an indent region 167 in the support structure 122 between the machined slots 166a and 166b. As shown in FIG. 11H, the indent region 167 can include a slit 169 positioned to allow separate portions of the indent region 167 to be depressed into the interior of the support structure 122. The indent region 167, for example, can be depressed into the passageway of the support structure 122 to hold the tuned control member 168 into place via the adhesive 164 and the control wire tip 173. The tuned control member 168, for example, can be routed below the indent region 167 (FIG. 11I) or above the indent region 167 (FIG. 11J). In some embodiments, the configuration of FIGS. 11E-11J can be suitable for the elongated shaft 16 (FIG. 1) when constructed of a material that is generally rigid in nature and that can be machined, such as stainless steel.

Figure 12A:
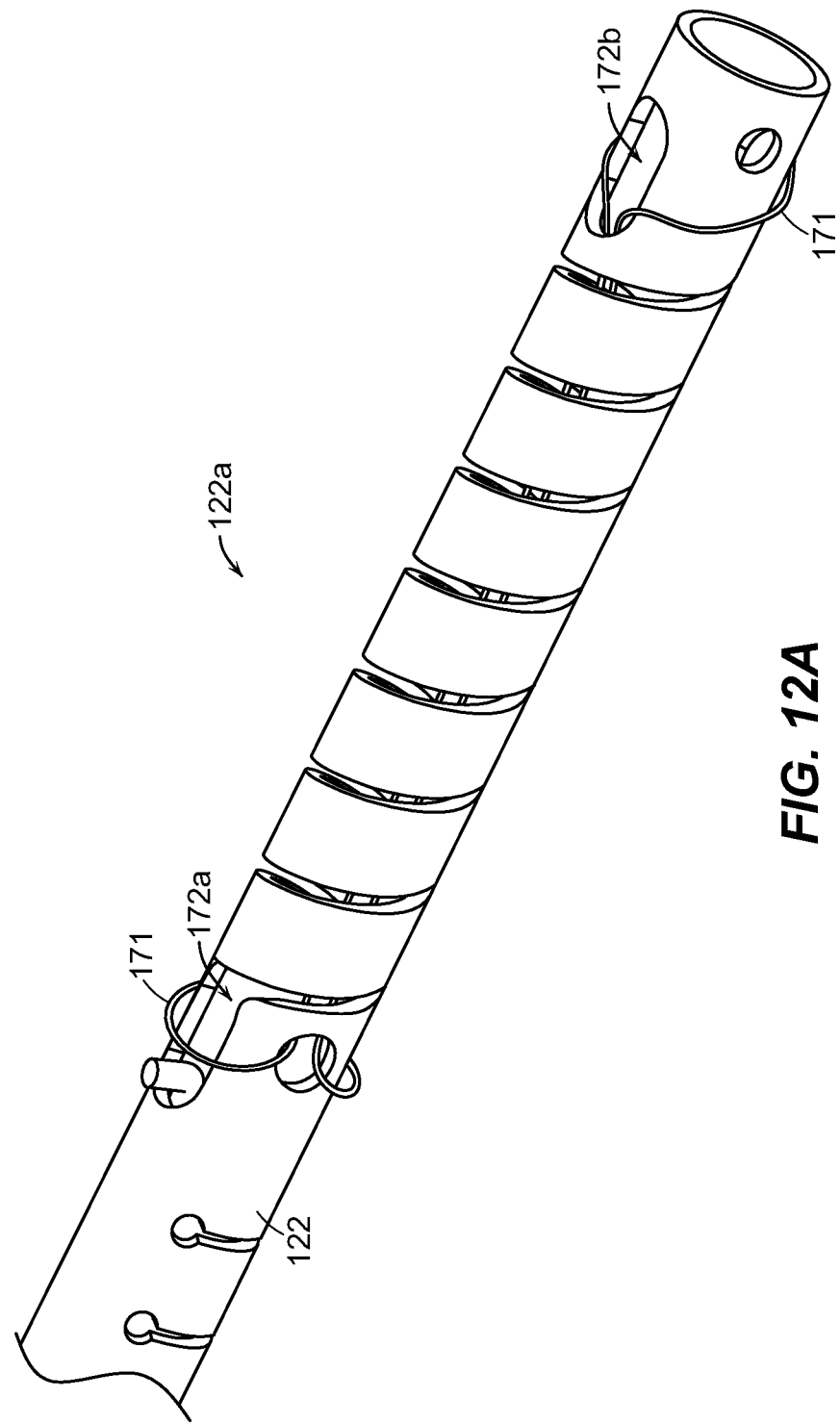
FIGS. 12A and 12B illustrate a restraint member configured to tether a distal portion of the support structure in accordance with embodiments of the present technology.
Figure 12B:
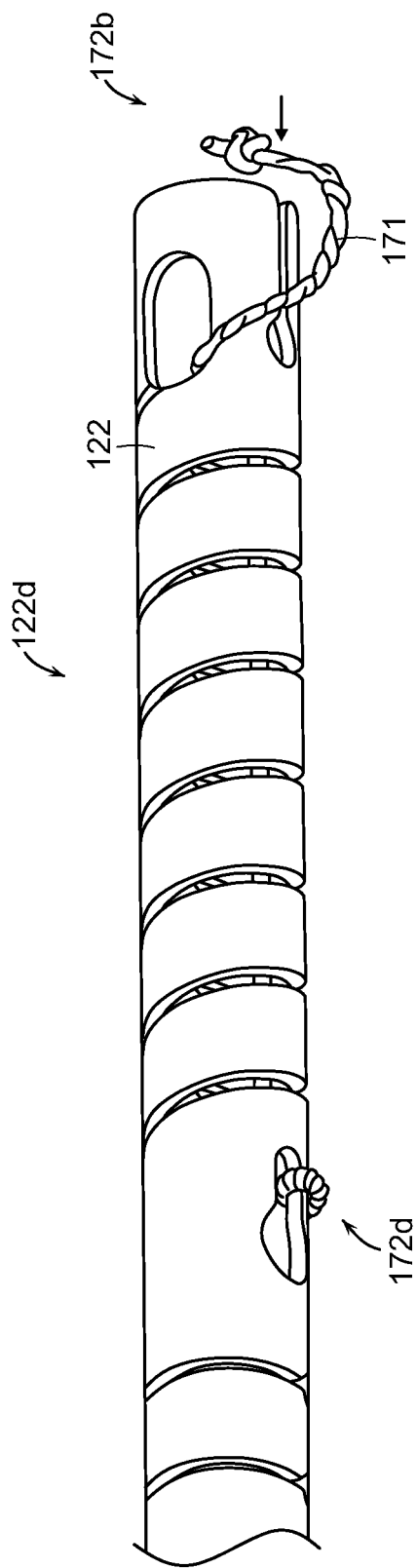

Referring back to FIG. 8, under some operating conditions, it may be possible for the distal deflection region 122a of the support structure 122 to become stretched or deformed during removal of the treatment device 112 from the patient anatomy. For example, when the treatment device 112 is removed through a guide catheter, the distal deflection region 122a can deform as it is pulled against the interior walls of the catheter, including, in particular, the bent portions of the catheter. To prevent this, a restraint member can tether the distal deflection region 122a of the support structure 122. Referring to FIGS. 12A and 12B together, for example, a restraint member 171 can extend through the distal deflection region 122a of the support structure 122 and be attached at anchoring regions 172a and 172b. As shown, the anchoring regions 172a and 172b include openings or holes formed through the body of the support structure 122. The restraint member 171 can include a wire, tube, or other suitable structure configured to inhibit or restrain deflection. The length of the restraint member 171 can be selected such that the restraint member 171 comprises an amount of slack when not flexed. This slack, for example, can allow the distal deflection region 122a to deflect by a pre-determined amount until the distal deflection region 122a is displaced beyond a threshold amount of deflection. A greater amount of slack can lessen the amount of restrain on the distal deflection region 122a and increase deflection, whereas a lesser amount of slack can increase the amount of restraint on the distal deflection region 122a and decrease deflection.

As shown in FIG. 12A, the restraint member 171 can be wrapped or looped through the holes at the anchoring regions 172a and 172b. In the alternate embodiment shown in FIG. 12B, the restraint member 171 can be knotted at each of the ends of the restraint member 171 so that the knots causes the restraint member to tighten when the support structure 122 is bent beyond a certain amount of deflection. In some embodiments, the knotted portions can be melted or glued at the anchoring regions 172a and 172b. In still other embodiments, other suitable techniques may be used to secure the restraint member 171 at the anchoring regions 172a and 172b.

Referring back to FIG. 8, the tuned control member 168 can extend through the elongated shaft 116 to the handle 134. In operation of the handle 134 to tension and release the tuned control member 168 when transforming the therapeutic assembly between deployed and delivered states, friction occurs between the (moving) tuned control member 168 and the interior of the relatively stationary elongated shaft 116. In one embodiment of the present technology, the tuned control member 168 may be configured to minimize the friction contact between the tuned control member 168 and the interior of the elongated shaft 116. For example, as shown in FIG. 8, a sleeve 170 can be disposed and at least partially bound to the tuned control member 168 to provide a relatively low-friction outer surface. The sleeve 170 preferably has axial length that is less than that of the elongated shaft 116 and, more preferably, covers a substantially proximal portion of the tuned control member 168 within the elongated shaft 116. During operation of the handle 134 to tension and release the tuned control member 168, the sleeve 170 is configured to move with the tuned control member 168 and acts as a bearing surface against the interior of the elongated shaft 116, thereby reducing friction between the tuned control member 168 and the elongated shaft 116. The sleeve 170 is an optional component that may not be used in some embodiments of the present technology.

In several embodiments, a control member (not shown) may be configured to be outside of the support structure of the treatment assembly that carries the energy delivery elements. For example, the support structure of the treatment assembly may instead be externally wound or wrapped around the control member. In such arrangements, the control member engages a portion of the support structure to apply a force that converts the support structure and the treatment assembly between its delivery and deployed state.

In one embodiment, the support structure 122 may be formed from a metallic shape-memory material (e.g., nitinol). Further, in one particular embodiment the support structure 122 can have an axial length of less than 12.7 cm (5 inches) and, more specifically, about 5.08 cm (2 inches); an outer diameter of about 0.57 mm (0.020 inch) and, more specifically, ranging between about 0.41 mm (0.016 inch) to about 0.46 mm (0.018 inch); a tubular wall thickness of less than 0.13 mm (0.005 inch) and, more particularly, about 0.08 mm (0.003 inch). In several embodiments, the elongated shaft 116 can be formed, at least in part, from stainless steel metal tubing having an outer diameter of, e.g., about 0.57 mm (0.020 inch) to about 1.52 mm (0.060 inch). In coupling the proximal portion of the support structure 122 to the stainless steel portion of the elongated shaft 116, a joint 119 may be provided therebetween to provide the desired transfer of torque from the stainless steel portion of the elongated shaft 116 to the support structure 122 when navigating to the treatment site. More specifically, each end of the support structure 122 and the stainless steel portion of the elongated shaft 116 may respectively include mating notches that permit the ends of the tubular members to interlock with one another. In some embodiments, disposed about the joint 119 is a stainless steel sleeve that is crimped about the juncture to provide additional support to the joint 119.

Figures 13A, 13B:
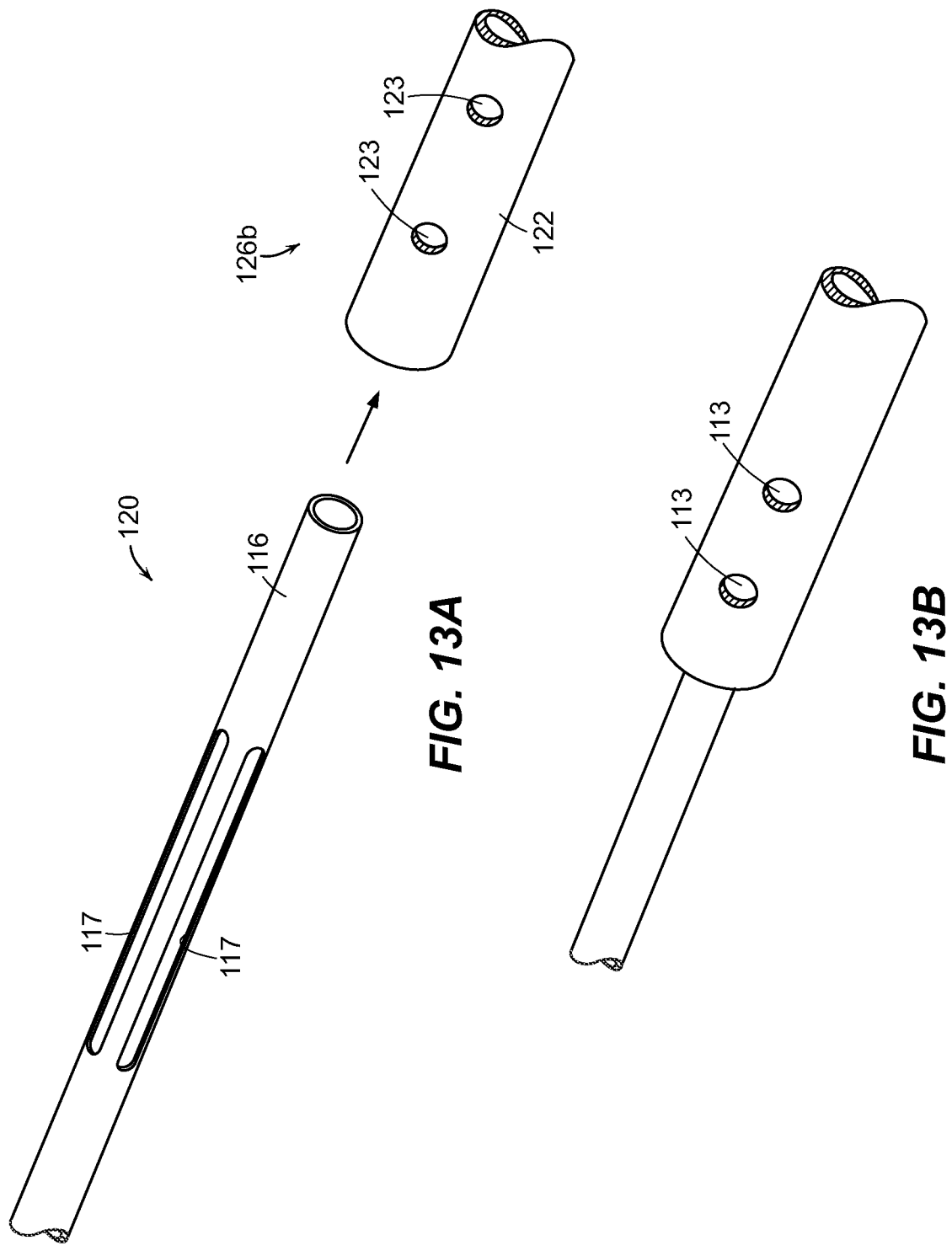

In other embodiments, the support structure 122 can be joined differently to the stainless steel portion of the elongated shaft 116. For example, as shown in FIGS. 13A and 13B, the proximal region 126b of the support structure 122 can be attached to the stainless steel portion of the elongated shaft 116 through one or more solder joints 113. The proximal region 126b of the support structure 122 can include one or more openings or holes 123 that align with grooves 117 in the distal region of the elongated shaft 116. When the support structure 122 is inserted into the lumen of the elongated shaft 116, the solder joints 113 can be formed by melting solder into the remaining lumen space between the deflector and the inside surface of the elongated shaft 116.

FIGS. 13C and 13D show the elongated shaft 116 configured in accordance with another embodiment of the present technology. Similar to the elongated shaft 116 of FIGS. 13A and 13B, the elongated shaft 116 can include a stainless steel portion. However, the configuration can be different in that the elongated shaft 116 employs a solderless connection. In this embodiment, for example, the support structure 122 includes locking features 127a and 127b that correspond with locking tabs 115a and 115b on the elongated shaft 116. The proximal region 126b of the support structure 122 can be inserted into the elongated shaft 116 until the locking features 127a and 127b align with the locking tabs 115a and 115b, respectively. The support structure 122 can be rotated about its longitudinal axis until the locking tabs 115a and 115b engage the corresponding locking features 127a and 127b. As shown, the proximal region 126b of the support structure 122 can also be configured with a tapered end to aid in alignment. In other embodiments, however, the proximal region 126b may have a different arrangement and/or include different features.

V. PERTINENT ANATOMY AND PHYSIOLOGY

The following discussion provides further details regarding pertinent patient anatomy and physiology. This section is intended to supplement and expand upon the previous discussion regarding the relevant anatomy and physiology, and to provide additional context regarding the disclosed technology and the therapeutic benefits associated with renal denervation. For example, as mentioned previously, several properties of the renal vasculature may inform the design of treatment devices and associated methods for achieving renal neuromodulation via intravascular access, and impose specific design requirements for such devices. Specific design requirements may include accessing the renal artery, facilitating stable contact between the energy delivery elements of such devices and a luminal surface or wall of the renal artery, and/or effectively modulating the renal nerves with the neuromodulatory apparatus.

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympathoadrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

Figure 14:
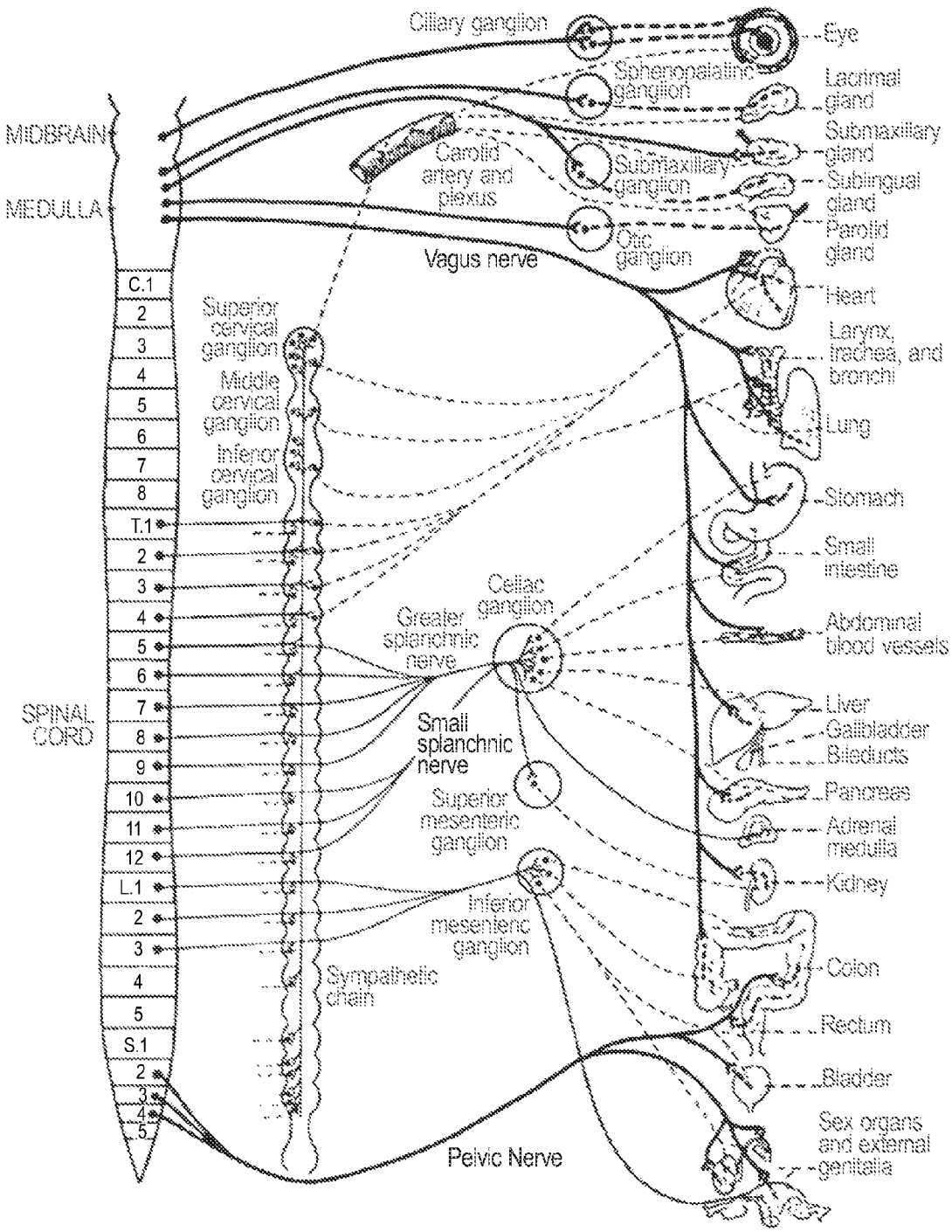
FIG. 14 is a conceptual illustration of the sympathetic nervous system (SNS) and how the brain communicates with the body via the SNS.

As shown in FIG. 14, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 15:
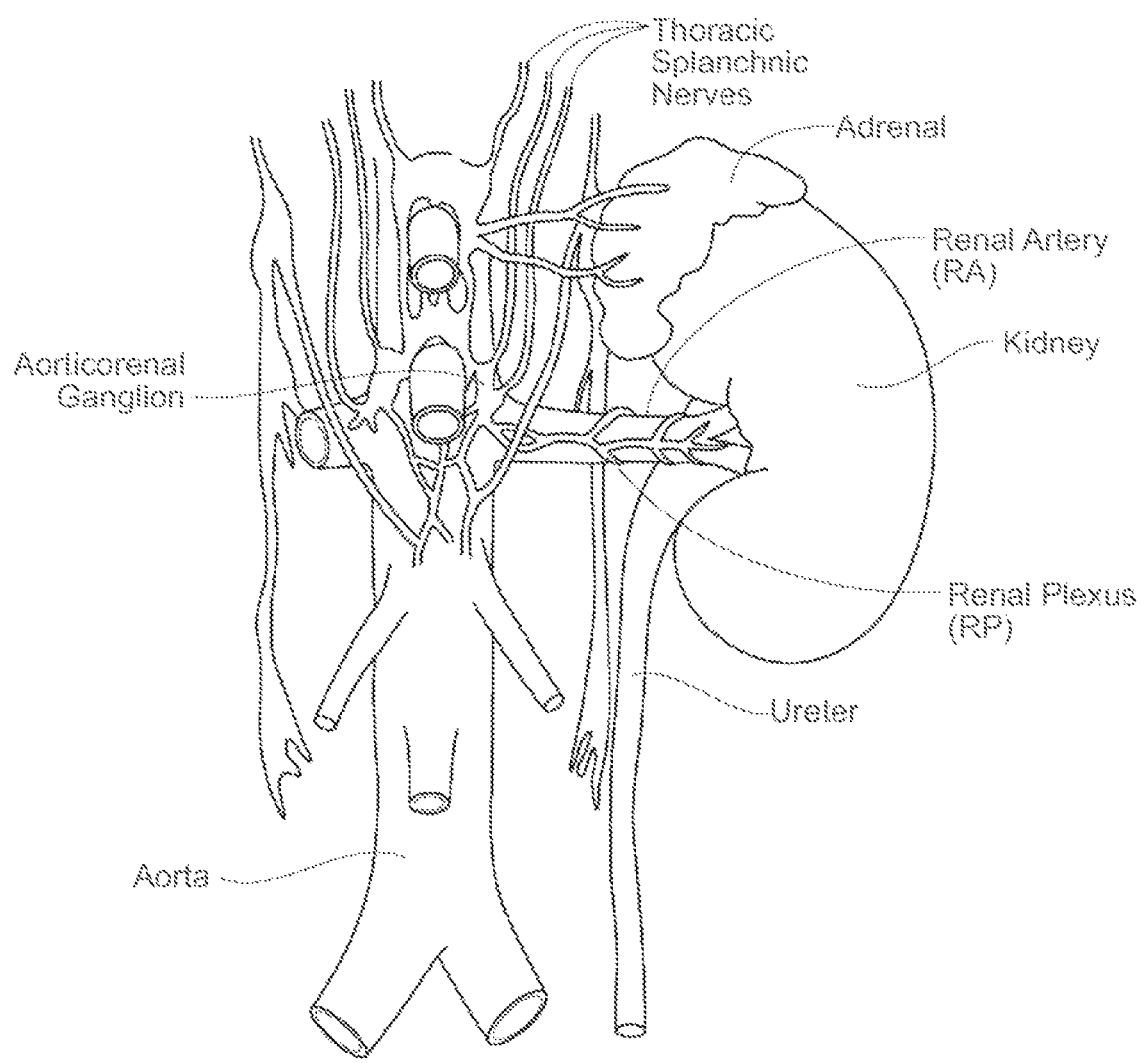
FIG. 15 is an enlarged anatomic view of nerves innervating a left kidney to form the renal plexus surrounding the left renal artery.

As shown in FIG. 15, the kidney is innervated by the renal plexus RP, which is intimately associated with the renal artery. The renal plexus RP is an autonomic plexus that surrounds the renal artery and is embedded within the adventitia of the renal artery. The renal plexus RP extends along the renal artery until it arrives at the substance of the kidney. Fibers contributing to the renal plexus RP arise from the celiac ganglion, the superior mesenteric ganglion, the aorticorenal ganglion and the aortic plexus. The renal plexus RP, also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus RP and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 16A:
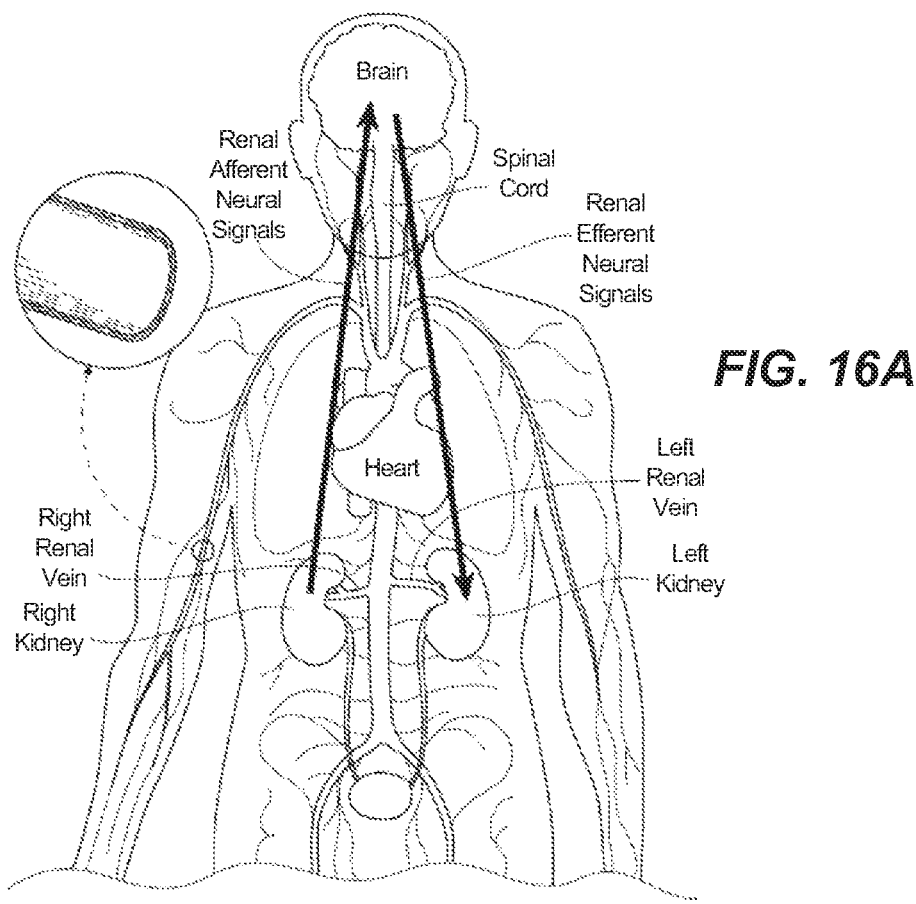
FIGS. 16A and 16B provide anatomic and conceptual views of a human body, respectively, depicting neural efferent and afferent communication between the brain and kidneys.
Figure 16B:
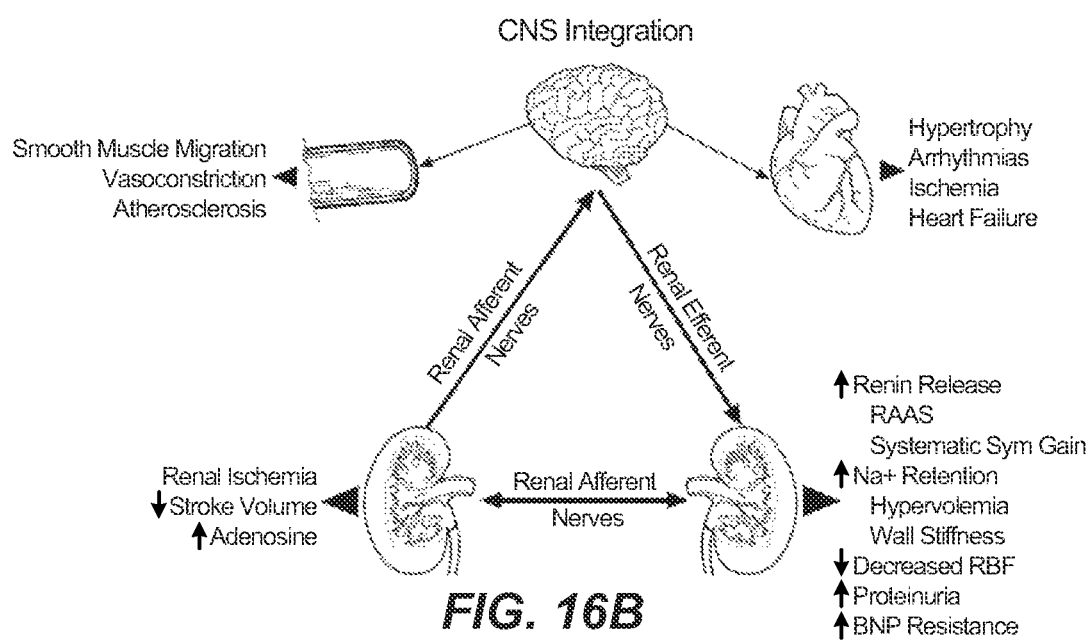

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 16A and 16B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIGS. 16A and 16B. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figures 17A, 17B:
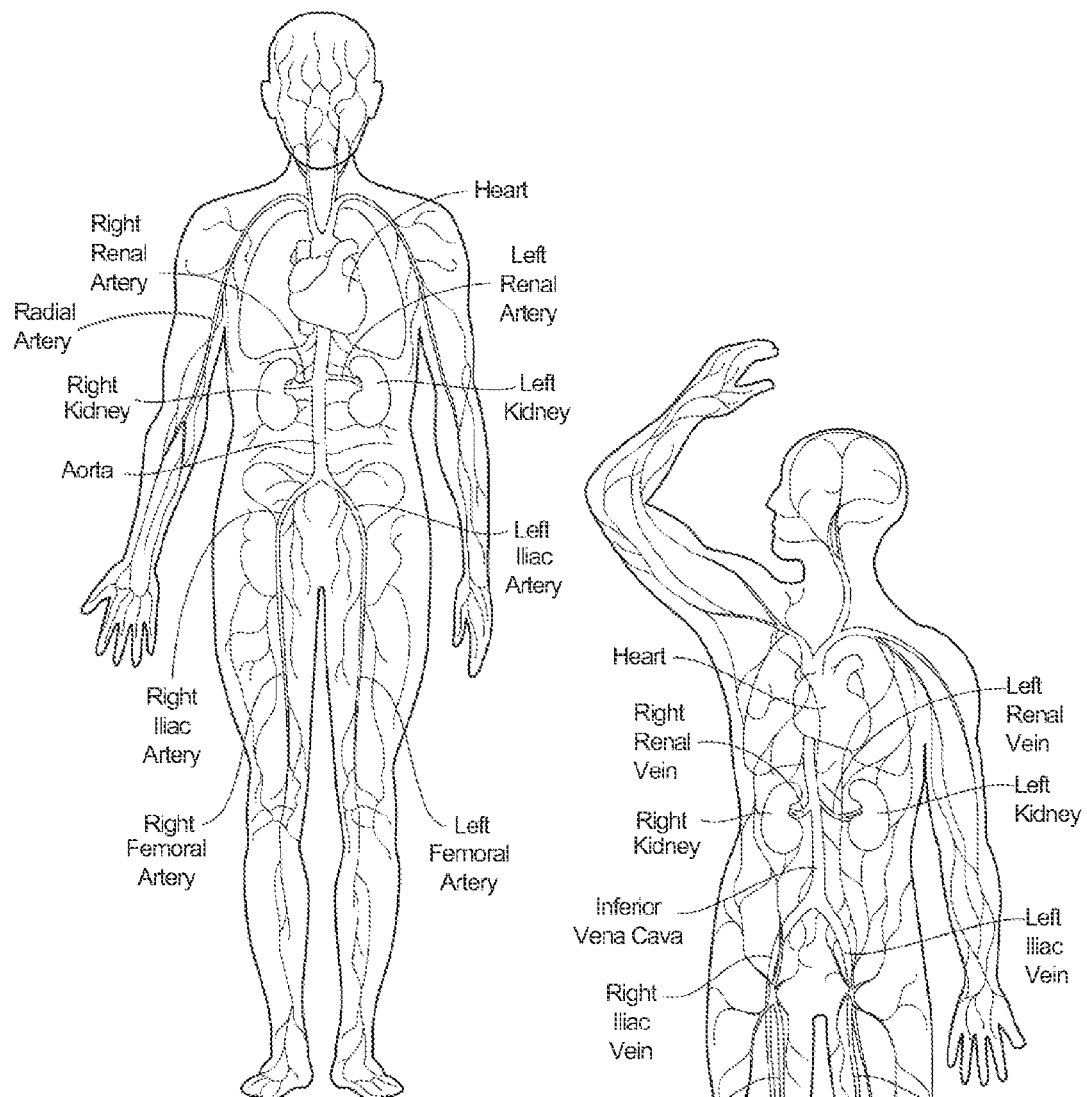
FIGS. 17A and 17B are, respectively, anatomic views of the arterial and venous vasculatures of a human.

In accordance with the present technology, neuromodulation of a left and/or right renal plexus RP, which is intimately associated with a left and/or right renal artery, may be achieved through intravascular access. As FIG. 17A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

As FIG. 17B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

The femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus RP may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. When the neuromodulatory apparatus includes an energy delivery element, such as an electrode, consistent positioning and appropriate contact force applied by the energy delivery element to the vessel wall are important for predictability. However, navigation is impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e., cause the wall of the artery to pulse).

Even after accessing a renal artery and facilitating stable contact between neuromodulatory apparatus and a luminal surface of the artery, nerves in and around the adventitia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, full-circle lesion likely resulting from a continuous circumferential treatment may be potentially related to renal artery stenosis. Therefore, the formation of more complex lesions along a longitudinal dimension of the renal artery via the mesh structures described herein and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility: and (f) as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, $D_{RA}$, typically is in a range of about 2-10 mm, with most of the patient population having a $D_{RA}$ of about 4 mm to about 8 mm and an average of about 6 mm. Renal artery vessel length, $L_{RA}$, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta, induced by respiration and/or blood flow pulsatility. A patient's kidney, which located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

VI. CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A catheter apparatus, comprising:
    an elongated tubular shaft having a proximal portion and a distal portion;
    a therapeutic assembly at the distal portion of the elongated shaft and transformable between a delivery state and a deployed state;
    a handle coupled to the proximal portion of the shaft;
    an actuator carried by the handle; and
    a tuned control member operably coupled between the actuator and the therapeutic assembly, wherein the tuned control member comprises a control wire extending through a lumen in the shaft and a tuning component coupled to the wire,
    wherein, when subjected to a tensile force—
        the control wire alone has a first force/displacement curve having a first superelastic response plateau at a first displacement along the first force/displacement curve,
        the tuned control member has a second force/displacement curve having a second superelastic response plateau at a second displacement along the second force/displacement curve less than the first displacement.

2. The catheter apparatus of claim 1 wherein the tuning component comprises a tube extending through a portion of the shaft, and wherein a portion of the control wire extends through the tube and is attached to the tube at one or more anchoring locations.

3. The catheter apparatus of claim 2 wherein the tube comprises an elasticity different than an elasticity of the control wire.

4. The catheter apparatus of claim 2 wherein the tube is composed of stainless steel and the control wire is composed of nitinol.

5. The catheter apparatus of claim 1 wherein the tuning component comprises a spring.

6. The catheter apparatus of claim 5 wherein the spring is positioned within the handle.

7. The catheter apparatus of claim 1 wherein the tuning component is coupled to a proximal end of the control wire.

8. The catheter apparatus of claim 1 wherein the tuning component is coupled to the control wire between a proximal end of the control wire and a distal end of the control wire.

9. The catheter apparatus of claim 1 wherein the control wire is composed of a superelastic material.

10. The catheter apparatus of claim 9 wherein the control wire is composed of nitinol.

11. The catheter apparatus of claim 1 wherein the tuned control member is coupled to a first attachment location at the therapeutic assembly and a second attachment location at the actuator.

12. The catheter apparatus of claim 1 wherein a first tensile force represented by the first superelastic response plateau of the first force/displacement curve is the same as a second tensile force represented by the second superelastic response plateau of the second force/displacement curve.

13. The catheter apparatus of claim 1 wherein a first tensile force represented by the first superelastic response plateau of the first force/displacement curve is greater than a second tensile force represented by the second superelastic response plateau of the second force/displacement curve.

14. A catheter apparatus, comprising:
    an elongated tubular shaft having a proximal portion and a distal portion;
    a treatment assembly at the distal portion of the elongated shaft and transformable between a low profile delivery arrangement and an expanded deployed arrangement;
    a handle coupled to the proximal portion of the shaft;
    an actuator at the handle and operably coupled to the treatment assembly via a tuned control member extending through the shaft, wherein the tuned control member comprises a control wire and a tuning component attached to one another within the shaft,
    wherein the tuning component is configured to selectively modify a stress-strain response of the control wire such that, when a tensile force is applied to the tuned control wire via the actuator to transform the treatment assembly from the delivery arrangement to the deployed arrangement, a plateau in a first force/displacement curve of the tuned control wire begins at a smaller displacement value along the first force/displacement curve of the tuned control wire than a plateau in a second force/displacement curve of a non-tuned control wire.

15. The catheter apparatus of claim 14 wherein the shaft has a first length and the control wire alone has a second length less than the first length.

16. The catheter apparatus of claim 14 wherein the tuning component is composed of a first material and the control wire is composed of a second material different than the first material, and wherein an elasticity of the second material is greater than an elasticity of the first material.

17. The catheter apparatus of claim 14 wherein the tuning component comprises a tubular member configured to receive at least a portion of the control wire, and wherein the control wire is composed of nitinol and the tubular member is composed of stainless steel.

18. The catheter apparatus of claim 14 wherein:
    the first force/displacement curve of the tuned control wire comprises (a) a first generally linear elastic force response over a first displacement range, and (b) a generally constant force response over a second displacement range, and
    the second force/displacement curve of the non-tuned control wire comprises (c) a second generally linear elastic force response over a third displacement range different than the first elastic force response over the first displacement range, and (d) a generally constant force response over a fourth displacement range different than the second displacement range.

19. The catheter apparatus of claim 18 wherein the first displacement range is less than the third displacement range.

20. The catheter apparatus of claim 18 wherein the second displacement range is less than the fourth displacement range.

* * * * *